United States Patent [19]

Tsubata et al.

[11] Patent Number: 5,104,872

[45] Date of Patent: Apr. 14, 1992

[54] N-(SUBSTITUTED BENZYLOXY) IMINE DERIVATIVES AND METHOD OF USE THEREOF

[75] Inventors: Kenji Tsubata; Nobuyuki Niino, both of Ibaraki; Katsutoshi Endo; Yoshinobu Yamamoto, both of Kawachinagano; Hideo Kanno, Ibaraki, all of Japan

[73] Assignee: Nihon Hohyaku Co., Ltd., Tokyo, Japan

[21] Appl. No.: 567,525

[22] Filed: Aug. 15, 1990

[30] Foreign Application Priority Data

Aug. 22, 1989 [JP] Japan .................. 1-215684

[51] Int. Cl.$^5$ ............... C07D 243/08; C07D 295/125; C07D 279/12; C07D 223/04; C07D 207/06; C07D 211/14; C07D 217/04

[52] U.S. Cl. .................. 514/238.2; 514/212; 514/227.8; 514/227.5; 514/235.8; 514/235.5; 514/256; 514/255; 514/307; 514/311; 514/314; 514/318; 514/278; 514/331; 514/343; 514/409; 514/428; 540/543; 540/601; 540/597; 540/610; 544/58.6; 544/58.5; 544/6; 544/58.1; 544/71; 544/122; 544/131; 544/162; 544/333; 544/360; 544/230; 544/399; 546/15; 546/145; 546/164; 546/235; 546/281; 548/409; 548/569

[58] Field of Search ........ 544/171, 58.1, 58.6, 544/131, 162, 360; 514/238.8, 227.5, 238.5, 239.2, 311, 331, 212, 428; 540/597, 610; 546/235, 164, 281; 548/409, 569, 238.2

[56] References Cited

U.S. PATENT DOCUMENTS

| | | | |
|---|---|---|---|
| 3,267,097 | 8/1966 | Kühle et al. | 548/569 |
| 3,336,186 | 8/1967 | Peissker et al. | 514/238.5 |
| 3,678,109 | 7/1972 | Knowles | 548/569 |
| 3,968,211 | 7/1976 | DuCharme | 514/238.5 |
| 4,465,678 | 8/1984 | Knops et al. | 540/610 |
| 4,723,034 | 2/1988 | Schirmer et al. | 560/60 |

FOREIGN PATENT DOCUMENTS

| | | |
|---|---|---|
| 0082059 | 6/1983 | European Pat. Off. |
| 0103957 | 3/1984 | European Pat. Off. |
| 178826 | 4/1986 | European Pat. Off. |
| 0184546 | 6/1986 | European Pat. Off. |
| 370629 | 5/1990 | European Pat. Off. |
| 2926408 | 1/1980 | Fed. Rep. of Germany |
| 61106538 | 5/1986 | Japan |
| 61-280452 | 12/1986 | Japan |
| 2042528 | 9/1980 | United Kingdom |
| 9007493 | 7/1990 | World Int. Prop. O. |

Primary Examiner—Mary C. Lee
Assistant Examiner—M. S. H. Gabilan
Attorney, Agent, or Firm—Browdy and Neimark

[57] ABSTRACT

Compound of the general formula (I), which is useful as an agricultural and horticultural fungicide, an agricultural and horticultural fungicidal composition containing said compound, use of said composition for controlling plant disease, and process for the production of said compound:

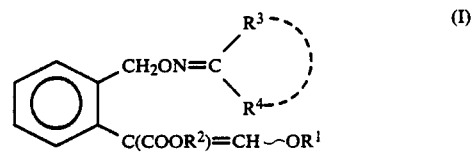

wherein

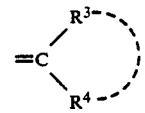

shows a case in which $R^3$ and $R^4$ together form a cyclic substituent, and $R^1$ and $R^4$ are substituents disclosed in the specification.

18 Claims, No Drawings

N-(SUBSTITUTED BENZYLOXY) IMINE DERIVATIVES AND METHOD OF USE THEREOF

BACKGROUND OF THE INVENTION

1. Field of the Invention

This invention relates to N-(substituted benzyloxy)imine derivatives, agricultural and horticultural fungicides containing them as an active ingredient, a process for the production thereof, and a controlling method.

2. Related Art

JP-A-61-280452 and JP, A-61-28045 disclose compounds which are structurally similar to the compound of this invention, and describe that such compounds are useful as a agricultural fungicide or insecticide. However, their activities cannot not necessarily be said to be satisfactory.

The compounds of this invention are novel compounds which have different substituents from those of these known compounds and have remarkable fungicidal activity over these known compounds.

DETAILED DESCRIPTION OF PREFERRED EMBODIMENTS

This invention relates to N-(substituted benzyloxy)imine derivatives of general formula

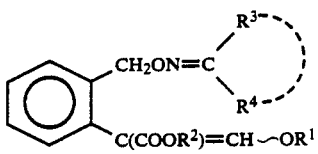

wherein $R^1$ and $R^2$ each independently represent a lower alkyl group, $R^3$ and $R^4$ each independently represent a hydrogen atom; a cyano group; a nitro group; an alkyl group; a haloalkyl group; a cycloalkyl group; an alkoxy group; a haloalkoxy group; an alkylthio group: a haloalkylthio group; an alkylsulfonyl group; an alkylsulfinyl group; an alkenylthio group; an alkynylthio group; an alkoxyalkyl group; an alkylthioalkyl group; a cycloalkylthio group; a lower alkoxycarbonylalkylthioalkyl group; phenyl group having 1 to 5 substituents which are independently selected from the class consisting of hydrogen atoms, halogen atoms, cyano groups, nitro groups, lower alkyl groups, lower haloalkyl groups, lower alkoxy groups, lower haloalkoxy groups, lower alkylthio groups, lower haloalkylthio groups, amino groups having a substituent or substituents which are independently selected from hydrogen atoms, formyl groups, lower alkyl groups and lower alkylcarbonyl groups, lower alkoxycarbonyl groups, mono- or di-lower alkylaminocarbonyl groups, mono- or di-lower alkylaminocarbonyloxy groups, methylenedioxy groups, phenyl groups having 1 to 5 substituents which are independently selected from hydrogen atoms, halogen atoms, lower alkyl groups and lower haloalkyl groups, phenoxy groups having 1 to 5 substituents which are independently selected from hydrogen atoms, halogen atoms, cyano groups, nitro groups, lower alkyl groups and lower haloalkyl groups, morpholino group which may have a substituent or substituents which are independently selected from lower alkyl groups, pyrimidyloxy groups which may have a substituent or substituents which are independently selected from lower alkyl groups, and morpholinocarbonyl groups which may have a substituent or substituents which are independently selected from lower alkyl groups; a phenoxyalkyl group having 1 to 5 substituents which are independently selected from hydrogen atoms, halogen atoms, lower alkyl groups and lower haloalkyl groups; a phenylthio group having 1 to 5 substituents which are independently selected from hydrogen atoms, halogen atoms, lower alkyl groups and lower haloalkyl groups; a phenylalkylthio group having 1 to 5 substituents which are independently selected from hydrogen atoms, halogen atoms, lower alkyl groups and lower haloalkyl groups; a phenylsulfonyl group having 1 to 5 substituents which are independently selected from hydrogen atoms, halogen atoms, lower alkyl groups and lower haloalkyl groups; a phenylthioalkyl group having 1 to 5 substituents which are independently selected from hydrogen atoms, halogen atoms, lower alkyl groups and lower haloalkyl groups; a phenylalkylthioalkyl group having 1 to 5 substituents which are independently selected from hydrogen atoms, halogen atoms, lower alkyl groups and lower haloalkyl groups; an aminoalkyl group having a substituent or substituents which are independently selected from hydrogen atoms, lower alkyl groups, lower haloalkyl groups, phenyl groups and benzyl groups; a furfurylthio group; a furfurylthioalkyl group; a morpholinoalkyl group which may have a substituent or substituents which are independently selected from lower alkyl groups; a $—CO—R^5$ group (in which $R^5$ represents a lower alkyl group; a lower haloalkyl group; a lower alkoxy group; a lower haloalkoxy group; a lower alkylthio group; a lower haloalkylthio group; an amino group having a substituent or substituents which are independently selected from hydrogen atoms, lower alkyl groups, lower haloalkyl groups and phenyl groups; a phenyl group having 1 to 5 substituents which are independently selected from hydrogen atoms, halogen atoms, cyano groups, nitro groups, lower alkyl groups, lower haloalkyl groups, lower alkoxy groups, lower haloalkoxy groups, lower alkylthio groups, lower haloalkylthio groups, lower alkylsulfinyl groups, lower haloalkylsulfinyl groups, lower alkylsulfonyl groups, lower haloalkylsulfonyl groups, lower alkoxyalkyl groups, amino groups having a substituent or substituents which are independently selected from hydrogen atoms, lower alkyl groups, lower alkylcarbonyl groups, lower haloalkylcarbonyl groups, lower alkylsulfonyl groups, lower haloalkylsulfonyl groups, lower alkoxycarbonyl groups and lower haloalkoxycarbonyl groups, phenyl groups having 1 to 5 substituents which are independently selected from hydrogen atoms, halogen atoms, lower alkyl groups and lower haloalkyl groups, phenoxy groups having 1 to 5 substituents which are independently selected from hydrogen atoms, halogen atoms, cyano groups, nitro groups, lower alkyl groups and lower haloalkyl groups, benzyl groups having 1 to 5 substituents which are independently selected from hydrogen atoms, halogen atoms, lower alkyl groups and lower haloalkyl groups, benzyloxy groups having 1 to 5 substituents which are independently selected from hydrogen atoms, halogen atoms, lower alkyl groups and lower haloalkyl groups, pyridyloxy groups having 1 to 4 substituents which are independently selected from hydrogen atoms, halogen atoms, lower alkyl groups and lower haloalkyl groups, methylenedioxy groups, and alkylene groups having 3 to 4 carbon atoms being attached to an adjacent carbon atoms; a benzyloxy group having 1 to 5 substituents which are independently selected from hydrogen atoms, halogen atoms, lower alkyl groups, lower haloalkyl groups, lower alkoxy groups, lower haloalkoxy groups, lower alkylthio groups and lower haloalkylthio groups; a naphthyl group; or a five- or six-membered hetero ring having 1 to 3 hetero atoms which are independently selected from oxygen atoms, sulfur atoms and nitrogen atoms and having, on the ring, a substituent or substituents selected from lower alkyl groups, lower haloalkyl groups, lower alkoxy groups and lower haloalkoxy groups); an amino group having a substituent or substituents which are independently selected from hydrogen atoms, lower alkyl groups, lower haloalkyl groups, lower alkenyl groups, lower alkynyl groups, lower alkoxyalkyl groups, lower dialkoxyalkyl groups, mono- or di-lower substituents which are independently selected from hydrogen atoms, halogen atoms, lower alkyl groups and lower haloalkyl groups, pyridylalkyl groups and morpholinoalkyl groups; a phenylalkyl group having 1 to 5 substituents which are independently selected from hydrogen atoms, halogen atoms, lower alkyl groups, lower haloalkyl groups, lower alkoxy groups, lower haloalkoxy groups, lower alkylthio groups and lower haloalkylthio groups; a phenylalkenyl group having 1 to 5 substituents which are independently selected from hydrogen atoms, halogen atoms, lower alkyl groups and lower haloalkyl groups; a naphthyl group; a lower dialkylphosphonyl group; or a 5 to 7 membered hetero ring having 1 to 3 hetero atoms which are independently selected from oxygen atoms, sulfur atoms and nitrogen atoms and having a substituent or substituents which are independently selected from hydrogen atoms, halogen atoms, cyano groups, nitro groups, lower alkyl groups, lower alkoxy groups, lower haloalkoxy groups, lower alkylthio groups, lower haloalkylthio groups, lower alkoxycarbonyl groups, phenyl groups having 1 to 5 substituents which are independently selected from hydrogen atoms and halogen atoms, benzyl groups, pyridyl groups, pyrimidyl groups and dioxolane groups, or a hetero ring thereof which is fused with benzene or cycloalkane or $R^3$ and $R^4$ together represent an alkylene or alkenylene group which may be interrupted with 1 to 3 atoms or groups selected from oxygen atoms, sulfur atoms, nitrogen atoms, carbonyl groups or nitrogen atoms having a substituent of a lower alkyl group or a phenyl group, and said group may have, on the alkylene or alkenylene chain, a substituent or substituents which are independently selected from lower alkyl groups, lower haloalkyl groups, lower alkoxy groups and lower haloalkoxy groups, and may be fused with a benzene ring to form a fused ring.

Preferred substituents on the N-(substituted benzyloxy)imine derivative of the general formula (I) are as follows. A methyl group is preferred as $R^1$ and $R^2$. Examples of $R^3$ and $R^4$ are preferably lower alkyl groups such as methyl and ethyl; lower alkoxy groups such as methoxy, ethoxy and propoxy; lower alkylthio groups such as methylthio, ethylthio and propylthio; lower alkoxyalkyl groups such as methoxymethyl, methoxyethyl and ethoxyethyl; phenyl groups having a substituent or substituents which are independently selected from halogen atoms such as chlorine, bromine and fluorine, lower alkyl groups such as methyl, ethyl and propyl, and lower haloalkyl groups such as difluoromethyl, trifluoromethyl and tetrafluoroethyl; phenylcarbonyl groups having, on the phenyl ring, a substituent or substituents which are independently selected from halogen atoms such as chlorine, bromine and fluorine, lower alkyl groups such as methyl, ethyl and propyl, lower haloalkyl groups such as difluoromethyl, trifluoromethyl and tetrafluoroethyl, and lower haloalkoxy groups such as difluoromethoxy, trifluoromethoxy and tetrafluoroethoxy; and morpholine having a substituent of a lower alkyl group such as methyl or ethyl.

As an illustrative example of the preferred N-(substituted benzyloxy)imine derivative the following compounds can be given. Those whose $R^1$ and $R^2$ are independently lower alkyl groups, and one of $R^3$ and $R^4$ is a lower alkyl group, a lower haloalkyl group or a lower alkoxyalkyl group and the other is a 5 to 7-membered hetero ring having 1 to 3 hetero atoms which are independently selected from oxygen atoms, sulfur atoms and nitrogen atom and having a 1 to 3 substituents which are independently selected from a hydrogen atom, a halogen atom, a cyano group, a nitro group, a lower alkyl group, a lower alkoxy group, a lower haloalkoxy group, a lower alkylthio group, a lower haloalkylthio group, a lower alkoxycarbonyl group, a phenyl group which may have 1 to 5 substituents selected independently from halogen atoms, benzyl groups, pyridyl groups, pyrimidyl groups and dioxolane groups, or a hetero ring thereof which is fused with benzene or cycloalkane.

As a more preferred compound having a hetero ring the followings can be given: Those whose hetero ring or said hetero ring thereof which is fused with benzene or cycloalkane is a pyrrolidine, piperidine, morpholine, thiomorpholine, piperazine, hexamethyleneimine, tetrahydroquinoline, tetrahydroisoquinoline, 2,3-dihydro-1,4-benzoxazine and the nitrogen atom in said hetero rings always forms the bond as a substituent of either $R^3$ or $R^4$. As a most preferred compound amongs N-(substituted benzyloxy)imine derivatives can be illustrated those having as $R^3$ or $R^4$ a morphino group which may be substituted with a lower alkyl group and the other is a lower alkyl group, a lower haloalkyl group, a lower alkoxyalkyl group, a phenyl group or a benzyl group.

Further preferred compounds are N-(substituted benzyloxy)imine derivatives having as the rest of either $R^3$ or $R^4$ a lower alkyl group or a lower haloalkyl group.

In this invention, the term "lower" defining substituents such as lower alkyl usually means that the substituent has 1 to 6 carbon atoms. For example, it should be understood that a "lower alkoxycarbonylalkylthioalkyl group" means an alkoxycarbonylalkylthioalkyl group having 4 to 19 carbon atoms (including carbon of the carbonyl group).

This invention, however, shall not be limited to the above-specified substituents.

The N-(substituted benzyloxy)imine derivative of this invention is present as an isomer having an E-form or Z-form with regard to the carbon-nitrogen double bonds and carbon-carbon double bonds, and these isomers and the mixture of them are included in the scope of this invention.

When a nitrogen atom is present in $R^3$ or $R^4$, the N-(substituted benzyloxy)imine derivative of this invention can be isolated as a quaternary salt thereof, e.g. as a salt of tosylate, etc.

The N-(substituted benzyloxy)imine derivative of the general formula (I) can be produced according to the following reaction scheme.

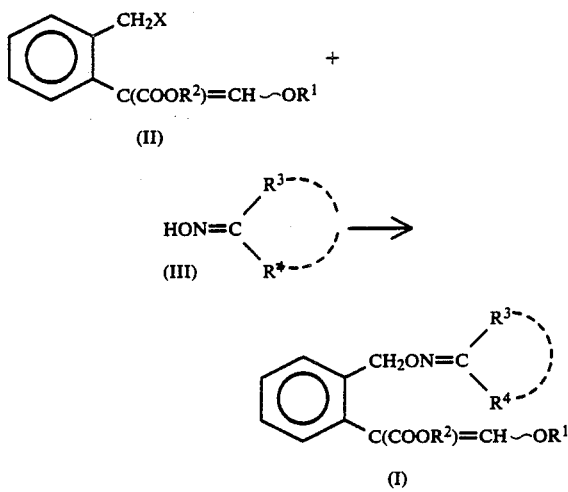

wherein $R^1$, $R^2$, $R^3$ and $R^4$ are as defined above, and X is halogen.

That is, the N-(substituted benzyloxy)imine derivative of the general formula can be produced by reacting a compound of the general formula (II) with a compound of the general formula (III) in the presence of a base or a silver compound and in the presence of an inert solvent.

Any inert solvent that does not prevent the present reaction can be used in this invention. Examples of such a solvent are alcohols such as isopropanol, tertbutanol and diethylene glycol; ketones such as acetone, methyl ethyl ketone and cyclohexanone, ethers such as diethyl ether, diisopropyl ether, tetrahydrofuran, dioxane, monoglyme, diglyme; halogenated hydrocarbons such as a dichloroethane, chloroform, carbon tetrachloride and tetrachloroethane; aromatic hydrocarbons such as benzene, chlorobenzene, nitrobenzene and toluene; nitriles such as acetonitrile; dimethylformamide; dimethylsulfoxide; water and a mixed solvent of these.

When a two-phase reaction is carried out in the mixed solvent, a phase transfer catalyst such as triethylbenzylammonium chloride, trioctylmethylammonium chloride or the like can be used.

Inorganic bases and organic bases are usable as a base. Examples of the inorganic bases are carbonates of alkali metals or alkaline earth metals such as sodium carbonate, potassium carbonate, calcium carbonate and sodium hydrogencarbonate; hydroxides of alkali metals or alkaline earth metals such as sodium hydroxide, potassium hydroxide and calcium hydroxide; and hydrides of alkali metals such as lithium hydride and sodium hydride. Examples of the organic bases are alkoxides of alkali metal atoms such as sodium methoxide and potassium tertbutoxide, diethylamine, triethylamine, pyridine, and benzyltrimethylammonium hydroxide.

As a silver compound, silver oxide and the like can be used.

The reaction temperature is suitably between $-70°$ C. and the boiling point of the solvent, and it is preferably between $-40°$ C. and $30°$ C. The reaction time varies depending upon the reaction temperature and the reaction scale. It is, in general, from 30 minutes to 12 hours.

The present reaction is an equimolar reaction, and a compound of the general formula (II) and a compound of the general formula (III) can be therefore used in equimolar amounts. However, one of these compounds may be used in an excess amount.

The base can be used in an equimolar amount based on a compound of the general formula (III). However, it may be used in an excess amount.

After completion of the reaction, the intended product is isolated by an ordinary method and, optionally, purified, e.g. by column chromatography or a recrystalization method.

The compound of the general formula (II) can be produced according to the process disclosed in JP, A 61-280452. The compound of the general formula (III), the scope of which includes some novel compounds, can be produced according to a process for the production of known compounds [e.g. Org. Syn. Coll. Vol. 2, 313 (1943), ditto, 363 (1943), and J. Org. Chem., 1980, 45. 4198].

Table 1 shows typical examples of the N-(substituted benzyloxy)imine derivative of the general formula (I). This invention, however, shall not be limited to these examples.

TABLE 1

| Compound No. | $R^1$ | $R^2$ | =C(R³)(R⁴) | Physical properties (melting point or refractive index) | *¹H-NMR Chemical shift |
|---|---|---|---|---|---|
| 1 | CH₃ | CH₃ | =CH—C₆H₅ | nD 1.5905 (18.9° C.) | 7.55 |
| 2 | CH₃ | CH₃ | =CH—C₆H₄(OCH₃) | nD 1.5895 (23.3° C.) | 7.52 |

TABLE 1-continued
| # | | | | | |
|---|---|---|---|---|---|
| 3 | CH₃ | CH₃ | 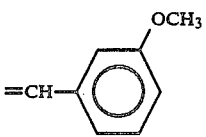 =CH—⌬—OCH₃ | nD 1.5905 (23.4° C.) | 7.53 |
| 4 | CH₃ | CH₃ |  =CH—⌬—OCH₃ | nD 1.5685 (23.5° C.) | 7.53 |
| 5 | CH₃ | CH₃ | 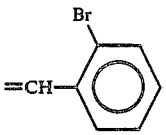 =CH—⌬(Br) | mp. 99.8–102.3° C. | 7.56 |
| 6 | CH₃ | CH₃ | 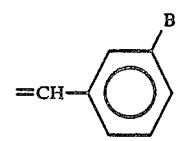 =CH—⌬(Br) | nD 1.5845 (23.9° C.) | 7.56 |
| 7 | CH₃ | CH₃ | 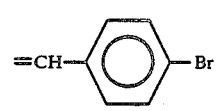 =CH—⌬—Br | mp. 137.7–141.2° C. | 7.50 |
| 8 | CH₃ | CH₃ | 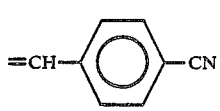 =CH—⌬—CN | mp. 157.8–160.6° C. | 7.56 |
| 9 | CH₃ | CH₃ | 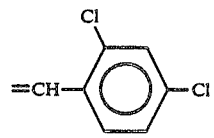 =CH—⌬(Cl,Cl) | mp. 106.9–111.8° C. | 7.56 |
| 10 | CH₃ | CH₃ | 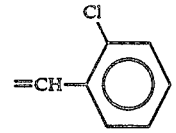 =CH—⌬(Cl) | mp. 95.4–96.6° C. | 7.54 |
| 11 | CH₃ | CH₃ | 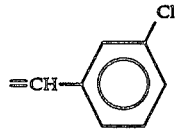 =CH—⌬(Cl) | nD 1.5919 (25.3° C.) | 7.61 |
| 12 | CH₃ | CH₃ | 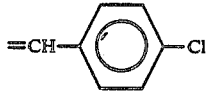 =CH—⌬—Cl | mp. 108.7– (dec.) | 7.57 |
| 13 | CH₃ | CH₃ | 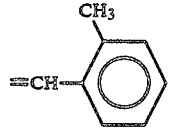 =CH—⌬(CH₃) | nD 1.5856 (21.0° C.) | 7.51 |
| 14 | CH₃ | CH₃ | 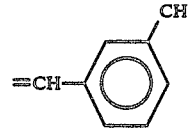 =CH—⌬—CH₃ | mp. 1.5726 (21.2° C.) | 7.54 |

TABLE 1-continued
| 15 | CH₃ | CH₃ | 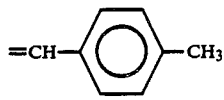 | nD 1.5827 (21.3° C.) | 7.53 |
| --- | --- | --- | --- | --- | --- |
| 16 | CH₃ | CH₃ | 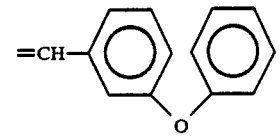 | nD 1.5978 (20.8° C.) | 7.54 |
| 17 | CH₃ | CH₃ | 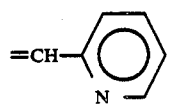 | nD 1.5890 (20.1° C.) | 7.57 |
| 18 | CH₃ | CH₃ | 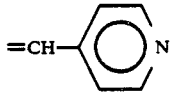 | mp. 111.6–113.2° C. | 7.57 |
| 19 | CH₃ | CH₃ | 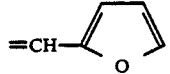 | nD 1.5778 (22.7° C.) | 7.40 |
| 20 | CH₃ | CH₃ | 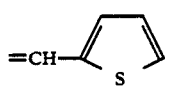 | nD 1.6016 (19.9° C.) | 7.53 |
| 21 | CH₃ | CH₃ | 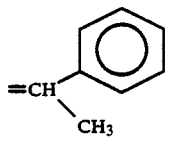 | nD 1.5869 (19.2° C.) | 7.57 |
| 22 | CH₃ | CH₃ | 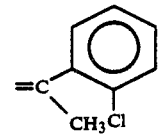 | nD 1.5613 (23.9° C.) | 7.49 |
| 23 | CH₃ | CH₃ | 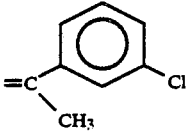 | nD 1.5815 (24.0° C.) | 7.52 |
| 24 | CH₃ | CH₃ | 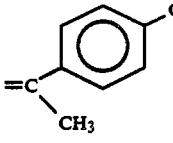 | mp. 106.1–112.5° C. | 7.48 |
| 25 | CH₃ | CH₃ | 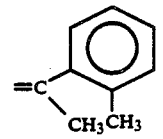 | nD 1.5717 (20.4° C.) | 7.51 |

TABLE 1-continued
| | | | | | |
|---|---|---|---|---|---|
| 26 | CH₃ | CH₃ | 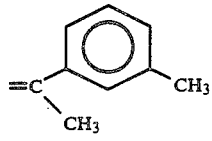 | nD 1.5765 (20.2° C.) | 7.55 |
| 27 | CH₃ | CH₃ | 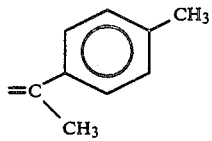 | nD 1.5757 (20.5° C.) | 7.52 |
| 28 | CH₃ | CH₃ | 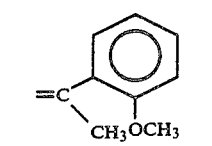 | nD 1.5690 (23.3° C.) | 7.53 |
| 29 | CH₃ | CH₃ | 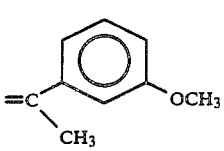 | nD 1.5780 (25.0° C.) | 7.53 |
| 30 | CH₃ | CH₃ | 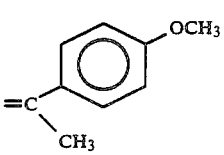 | nD 1.5880 (24.9° C.) | 7.53 |
| 31 | CH₃ | CH₃ | 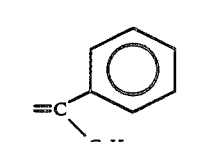 | nD 1.5788 (25.3° C.) | 7.55 |
| 32 | CH₃ | CH₃ | 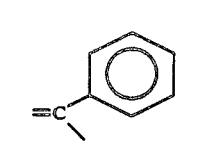 | nD 1.5735 (21.8° C.) | 7.53 |
| 33 | CH₃ | CH₃ | 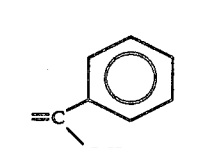 | nD 1.5690 (21.8° C.) | 7.56 |
| 34 | CH₃ | CH₃ | 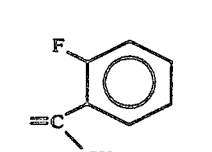 | nD 1.5670 (24.0° C.) | 7.53 |
| 35 | CH₃ | CH₃ | 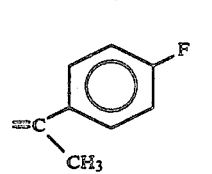 | nD 1.5745 (24.0° C.) | 7.53 |

TABLE 1-continued

| # | | | Structure | Property | Value |
|---|---|---|---|---|---|
| 36 | CH$_3$ | CH$_3$ | =C(phenyl)(CH$_2$OCH$_3$) | nD 1.5770 (22.1° C.) | 7.53 |
| 37 | CH$_3$ | CH$_3$ | =C(phenyl)(phenyl) | mp. 111–130° C. | 7.47 |
| 38 | CH$_3$ | CH$_3$ | =C(1-naphthyl)(CH$_3$) | mp. 118.1–122.6° C. | 7.56 |
| 39 | CH$_3$ | CH$_3$ | =C(2-furyl)(CH$_3$) | nD. 1.5767 (22.7° C.) | 7.50 |
| 40 | CH$_3$ | CH$_3$ | =C(2-thienyl)(CH$_3$) | nD. 1.5949 (20.8° C.) | 7.51 |
| 41 | CH$_3$ | CH$_3$ | =C(2-pyridyl)(CH$_3$) | nD. 1.5697 (22.2° C.) | 7.54 |
| 42 | CH$_3$ | CH$_3$ | =C(4-pyridyl)(CH$_3$) | nD. 1.5778 (22.7° C.) | 7.57 |
| 43 | CH$_3$ | CH$_3$ | =C(H)(COO-phenyl) | nD. 1.5877 (23.0° C.) | 7.58 |
| 44 | CH$_3$ | CH$_3$ | =C(CH$_3$)(COO-phenyl) | nD. 1.5716 (20.2° C.) | 7.55 |
| 45 | CH$_3$ | CH$_3$ | =C(H)(COO-2-pyridyl) | mp. 102.1–105.3° C. | 7.63 |

TABLE 1-continued

| | | | Structure | Properties | Value |
|---|---|---|---|---|---|
| 46 | CH$_3$ | CH$_3$ | =C(–CO–C$_6$H$_5$)(–C$_6$H$_5$) | nD 1.6091 (23.8° C.) | 7.52 |
| 47 | CH$_3$ | CH$_3$ | =CH–CO–C$_6$H$_4$–Cl | nD 1.5815 (25.5° C.) | 7.63 |
| 48 | CH$_3$ | CH$_3$ | =C(CH$_3$)–CO–C$_6$H$_4$–Cl | nD 1.5748 (25.5° C.) | 7.64 |
| 49 | CH$_3$ | CH$_3$ | =C(C$_2$H$_5$)–CO–C$_6$H$_5$ | nD 1.5719 (25.2° C.) | 7.53 |
| 50 | CH$_3$ | CH$_3$ | =C(CO–CH$_3$)–CO–C$_6$H$_5$ | nD 1.5763 (25.4° C.) | 7.51 |
| 51 | CH$_3$ | CH$_3$ | =C(CO–OC$_2$H$_5$)–CO–C$_6$H$_5$ | nD 1.5642 (25.5° C.) | 7.53 |
| 52 | CH$_3$ | CH$_3$ | =C(CO–CH$_3$)(CH$_3$) | mp. 82.7–84.6° C. | 7.63 |
| 53 | CH$_3$ | CH$_3$ | =C(CN)(CO–OC$_2$H$_5$) | mp. 91.9–94.8° C. | 7.65 |
| 54 | CH$_3$ | CH$_3$ | =C(CO–OC$_2$H$_5$)$_2$ | nD 1.5238 (25.2° C.) | 7.65 |
| 55 | CH$_3$ | CH$_3$ | =C(C$_6$H$_5$)(CN) | mp. 111.5–113.0° C. Rf. high | 7.61 |

TABLE 1-continued
| 56 | CH₃ | CH₃ | 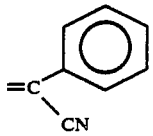 | nD. 1.5895 (22.8° C.) Rf. low | 7.61 |
| --- | --- | --- | --- | --- | --- |
| 57 | CH₃ | CH₃ | 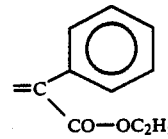 | nD. 1.5698 (22.9° C.) Rf. high | 7.59 |
| 58 | CH₃ | CH₃ | 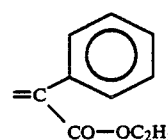 | mp. 77.3–81.3° C. Rf. high | 7.53 |
| 59 | CH₃ | CH₃ | 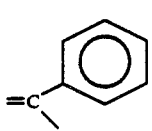 | nD. 1.5924 (18.6° C.) | 7.59 |
| 60 | CH₃ | CH₃ | 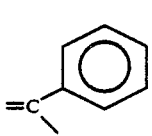 | nD. 1.5846 (18.4° C.) | 7.63 |
| 61 | CH₃ | CH₃ | 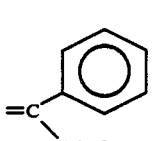 | nD. 1.5748 (20.1° C.) | 7.55 |
| 62 | CH₃ | CH₃ | 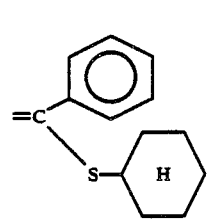 | nD. 1.5868 (20.2° C.) | 7.54 |
| 63 | CH₃ | CH₃ | 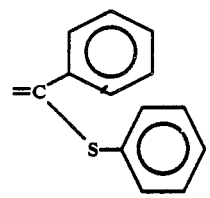 | Paste | 7.57 |
| 64 | CH₃ | CH₃ | 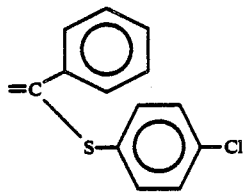 | nD. 1.6140 (20.0° C.) | 7.55 |

TABLE 1-continued

| 65 | CH₃ | CH₃ | =C(−C₆H₅)(SCH₃)−C₆H₅ (α-phenylthio-benzylidene) | nD 1.6162 (20.0° C.) | 7.53 |
|---|---|---|---|---|---|
| 66 | CH₃ | CH₃ | =C(−C₆H₅)−SCH₂−(2-furyl) | nD 1.5996 (20.1° C.) | 7.55 |
| 67 | CH₃ | CH₃ | =C(−4-CH₃−C₆H₄)(SCH₃) | mp. 99.8–105.3° C. | 7.50 |
| 68 | CH₃ | CH₃ | =C(−4-Cl−C₆H₄)(SCH₃) | mp. 114.3–117.5° C. | 7.57 |
| 69 | CH₃ | CH₃ | =C(−3-PhO−C₆H₄)(SCH₃) | nD 1.6073 (23.1° C.) | 7.52 |
| 70 | CH₃ | CH₃ | =C(−C₆H₅)(SC₂H₅) | nD 1.5917 (23.0° C.) | 7.54 |
| 71 | CH₃ | CH₃ | =C(CH₃)(SCH₃) | nD 1.5730 (20.1° C.) | 7.53 |
| 72 | CH₃ | CH₃ | =C(CH₃)(SC₃H₇−n) | nD 1.5561 (26.1° C.) | 7.53 |
| 73 | CH₃ | CH₃ | =C(CH₃)(S−cyclohexyl) | mp. 105.2–113.5° C. | 7.54 |
| 74 | CH₃ | CH₃ | =C(CH₃)(S−C₆H₅) | nD 1.5960 (21.2° C.) | 7.58 |

TABLE 1-continued

| No. | R1 | R2 | Structure | Properties | Value |
|---|---|---|---|---|---|
| 75 | CH₃ | CH₃ | =C(SCH₃)-(2-pyridyl) | nD 1.5912 (23.8° C.) | 7.49 |
| 76 | CH₃ | CH₃ | =C(S-C₆H₅)-(2-pyridyl) | nD 1.6158 (25.9° C.) | 7.58 |
| 77 | CH₃ | CH₃ | =C(SO₂-C₆H₄-4-CH₃)-(2,6-dichlorophenyl) | mp. 139.1–143.3° C. | 7.50 |
| 78 | CH₃ | CH₃ | =C(SCH₃)-(2-chlorophenyl) | nD 1.5899 (24.4° C.) | 7.55 |
| 79 | CH₃ | CH₃ | =C(SCH₃)-(3-chlorophenyl) | nD 1.5973 (25.0° C.) | 7.58 |
| 80 | CH₃ | CH₃ | =C(SCH₃)-(4-cyanophenyl) | mp. 108–110° C. | 7.58 |
| 81 | CH₃ | CH₃ | =C(SCH₃)-(4-trifluoromethylphenyl) | mp. 90–92° C. | 7.58 |
| 82 | CH₃ | CH₃ | =C(SCH₃)-(4-methoxyphenyl) | nD 1.5920 (25.0° C.) | 7.58 |
| 83 | CH₃ | CH₃ | =C(SCH₃)-(3-methoxyphenyl) | nD 1.5752 (24.9° C.) | 7.58 |

TABLE 1-continued

| | | | | | |
|---|---|---|---|---|---|
| 84 | CH$_3$ | CH$_3$ | =C(CO—OC$_2$H$_5$)(SCH$_3$) | nD 1.5572 (23.3° C.) | 7.60 |
| 85 | CH$_3$ | CH$_3$ | =C(SO$_2$—C$_6$H$_5$)(CN) | nD 1.5786 (23.8° C.) | 7.59 |
| 86 | CH$_3$ | CH$_3$ | =C(SO$_2$—C$_6$H$_5$)(CH$_3$) | nD 1.5755 (23.5° C.) | 7.57 |
| 87 | CH$_3$ | CH$_3$ | =C(C$_6$H$_5$)(NHCH$_2$) | Paste | 7.58 |
| 88 | CH$_3$ | CH$_3$ | =C(C$_6$H$_5$)(morpholino) | Paste | 7.53 |
| 89 | CH$_3$ | CH$_3$ | =C(CH$_3$)(NHCH$_3$) | Paste | 7.50 |
| 90 | CH$_3$ | CH$_3$ | =C(CH$_3$)(NHC$_3$H$_7$-i) | Paste | 7.52 |
| 91 | CH$_3$ | CH$_3$ | =C(CH$_3$)(morpholino) | Paste | 7.53 |
| 92 | CH$_3$ | CH$_3$ | =C(4-Cl-C$_6$H$_4$)(NHCH$_3$) | Paste | 7.50 |
| 93 | CH$_3$ | CH$_3$ | =C(SC$_2$H$_5$)(SC$_2$H$_5$) | nD 1.5770 (18.9° C.) | 7.58 |
| 94 | CH$_3$ | CH$_3$ | =C(SC$_3$H$_7$-i)(SC$_3$H$_7$-i) | nD 1.5665 (18.0° C.) | 7.53 |

TABLE 1-continued
| 95 | CH₃ | CH₃ | 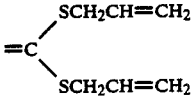 | Paste | 7.47 |
| 96 | CH₃ | CH₃ | 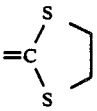 | nD 1.5917 (18.6° C.) | 7.53 |
| 97 | CH₃ | CH₃ | 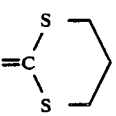 | Paste | 7.55 |
| 98 | CH₃ | CH₃ | 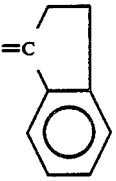 | nD 1.5990 (22.1° C.) | 7.53 |
| 99 | CH₃ | CH₃ |  | mp. 131.4–134.8° C. | 7.65 |
| 100 | CH₃ | CH₃ | 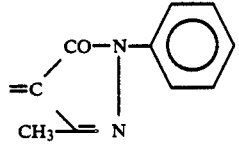 | mp. 131.4–134.8° C. | 7.65 |
| 101 | CH₃ | CH₃ | 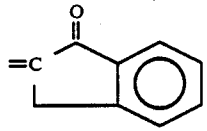 | mp. 117.6–121.5° C. | 7.67 |
| 102 | CH₃ | CH₃ | 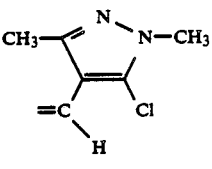 | mp. 108.9–114.7° C. | 7.53 |
| 103 | CH₃ | CH₃ | 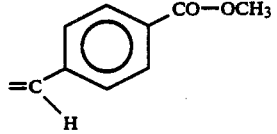 | mp. 141.9–145.6° C. | 7.53 |
| 104 | CH₃ | CH₃ | 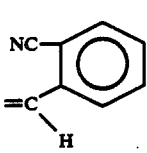 | mp. 149.0–153.0° C. | 7.53 |
| 105 | CH₃ | CH₃ | 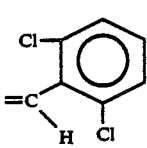 | mp. 130.2–153.0° C. | 7.53 |

TABLE 1-continued
| | | | | | |
|---|---|---|---|---|---|
| 106 | CH₃ | CH₃ | 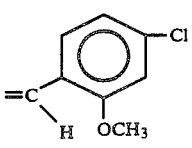 | mp. 84.6–90.0° C. | 7.50 |
| 107 | CH₃ | CH₃ | 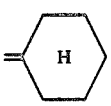 | nD 1.5401 (24.5° C.) | 7.50 |
| 108 | CH₃ | CH₃ | 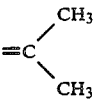 | nD 1.5351 (25.6° C.) | 7.53 |
| 109 | CH₃ | CH₃ | 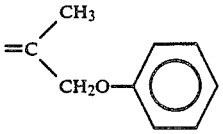 | nD 1.5570 (23.5° C.) | 7.53 |
| 110 | CH₃ | CH₃ | 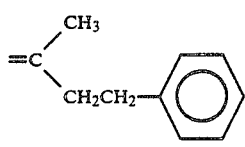 | nD 1.5586 (22.5° C.) | 7.50 |
| 111 | CH₃ | CH₃ | 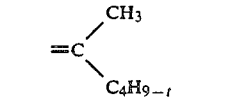 | nD 1.5192 (23.5° C.) | 7.49 |
| 112 | CH₃ | CH₃ | 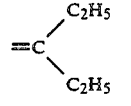 | nD 1.5304 (26.6° C.) | 7.50 |
| 113 | CH₃ | CH₃ | 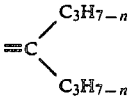 | nD 1.5218 (22.7° C.) | 7.52 |
| 114 | CH₃ | CH₃ | 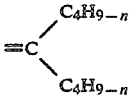 | nD 1.5179 (22.2° C.) | 7.50 |
| 115 | CH₃ | CH₃ | 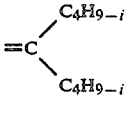 | nD 1.5014 (26.7° C.) | 7.55 |
| 116 | CH₃ | CH₃ | 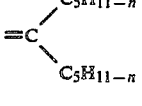 | nD 1.5100 (22.8° C.) | 7.48 |
| 117 | CH₃ | CH₃ | 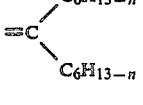 | nD 1.5068 (22.9° C.) | 7.48 |
| 118 | CH₃ | CH₃ | 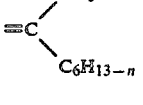 | nD 1.5090 (20.8° C.) | 7.49 |

TABLE 1-continued
| 119 | CH₃ | CH₃ | 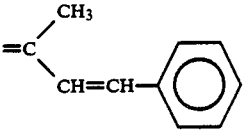 | nD 1.6110 (20.3° C.) | 7.52 |
| --- | --- | --- | --- | --- | --- |
| 120 | CH₃ | CH₃ | 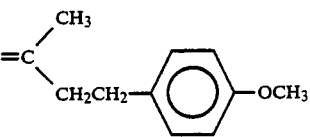 | nD 1.5587 (21.8° C.) | 7.50 |
| 121 | CH₃ | CH₃ | 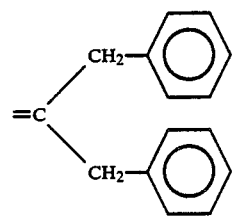 | nD 1.5788 (23.3° C.) | 7.54 |
| 122 | CH₃ | CH₃ | 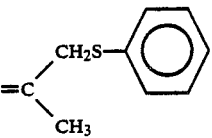 | nD 1.5806 (23.4° C.) | 7.48 |
| 123 | CH₃ | CH₃ | 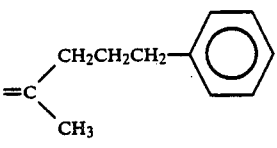 | nD 1.5592 (19.8° C.) | 7.49 |
| 124 | CH₃ | CH₃ | 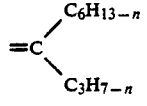 | nD 1.5169 (18.8° C.) | 7.46 |
| 125 | CH₃ | CH₃ | 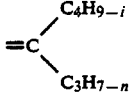 | nD 1.5217 (18.7° C.) | 7.44 |
| 126 | CH₃ | CH₃ | 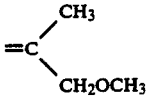 | mp. 51.1–54.6° C. | 7.52 |
| 127 | CH₃ | CH₃ | 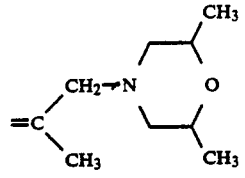 | nD 1.5324 (19.4° C.) (cis-form) | 7.52 |
| 128 | CH₃ | CH₃ | 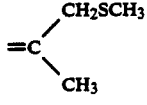 | nD 1.5575 (17.5° C.) | 7.50 |
| 129 | CH₃ | CH₃ | 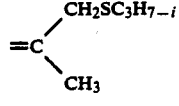 | nD 1.5450 (25.4° C.) | 7.50 |

TABLE 1-continued

| | | | | | |
|---|---|---|---|---|---|
| 130 | CH₃ | CH₃ | =C(CH₂SCH₃)(CH₂SCH₃) | Yellow paste | 7.53 |
| 131 | CH₃ | CH₃ | =C(CH(CH₃)SCH₃)(CH₂SCH₃) | nD 1.5465 (25.0° C.) | 7.50 |
| 132 | CH₃ | CH₃ | =C(CH₂CH₂CH₂SCH₃)(CH₃) | nD 1.5450 (21.8° C.) | 7.53 |
| 133 | CH₃ | CH₃ | =C(CH₂SCH₂-Ph)(CH₃) | nD 1.5875 (25.8° C.) | 7.53 |
| 134 | CH₃ | CH₃ | =C(CH₂-N(CH₃)-Ph)(CH₃) | nD 1.5810 (21.7° C.) | 7.56 |
| 135 | CH₃ | CH₃ | =C(CH₂-N(CH₃)-CH₂-Ph)(CH₃) | nD 1.5580 (21.4° C.) | 7.56 |
| 136 | CH₃ | CH₃ | =C(CH₂CH₂OC₂H₅)(CH₃) | nD 1.5350 (28.5° C.) | 7.50 |
| 137 | CH₃ | CH₃ | =C(CH₂CH₂OC₄H₉-i)(CH₃) | nD 1.5195 (18.6° C.) | 7.53 |
| 138 | CH₃ | CH₃ | =C(CH₂SCH₂-furyl)(CH₃) | Brown paste | 7.56 |
| 139 | CH₃ | CH₃ | =C (tetrahydropyranyl with CH₃) | nD 1.5400 (25.8° C.) | 7.56 |
| 140 | CH₃ | CH₃ | =C (tetrahydropyran) | nD 1.5551 (21.2° C.) | 7.50 |
| 141 | CH₃ | CH₃ | =C (thiane) | nD 1.5775 (21.3° C.) | 7.53 |

TABLE 1-continued
| | | | | | |
|---|---|---|---|---|---|
| 142 | CH₃ | CH₃ | 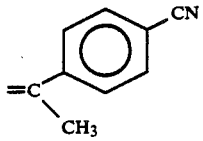 | mp. 122.5–127.1° C. | 7.56 |
| 143 | CH₃ | CH₃ | 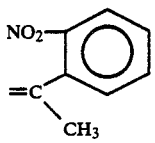 | Yellow paste | 7.56 |
| 144 | CH₃ | CH₃ | 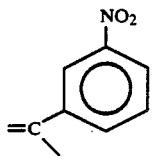 | Colorless paste | 7.53 |
| 145 | CH₃ | CH₃ | 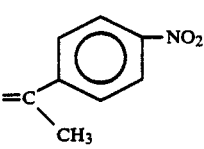 | mp. 122.5–126.4° C. | 7.53 |
| 146 | CH₃ | CH₃ | 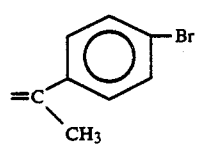 | mp. 116.8–121.3° C. | 7.53 |
| 147 | CH₃ | CH₃ | 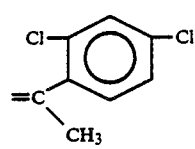 | Colorless paste | 7.53 |
| 148 | CH₃ | CH₃ | 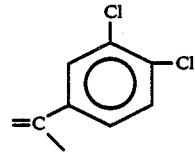 | Green paste | 7.53 |
| 149 | CH₃ | CH₃ | 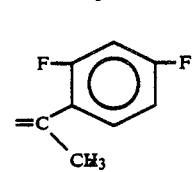 | m.p. 55.6–72.1° C. | 7.50 |
| 150 | CH₃ | CH₃ | 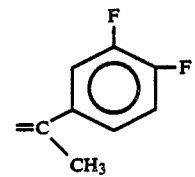 | nD 1.5680 (17.3° C.) | 7.53 |

-continued
| | | | | | |
|---|---|---|---|---|---|
| 151 | CH$_3$ | CH$_3$ | 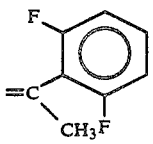 | m.p. 95.0–97.8° C. | 7.50 |
| 152 | CH$_3$ | CH$_3$ | 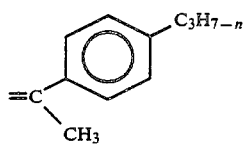 | mp. 85.5–88.5° C. | 7.53 |
| 153 | CH$_3$ | CH$_3$ | 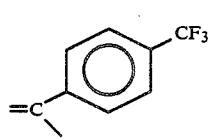 | mp. 115.5–121.9° C. | 7.53 |
| 154 | CH$_3$ | CH$_3$ | 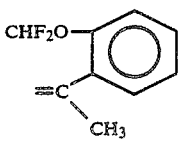 | nD 1.5540 (20.0° C.) | 7.50 |
| 155 | CH$_3$ | CH$_3$ | 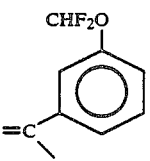 | nD 1.5590 (20.0° C.) | 7.50 |
| 156 | CH$_3$ | CH$_3$ | 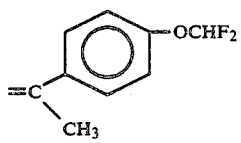 | mp. 99.6–100.8° C. | 7.56 |
| 157 | CH$_3$ | CH$_3$ | 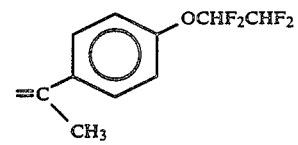 | nD 1.5390 (18.6° C.) | 7.56 |
| 158 | CH$_3$ | CH$_3$ | 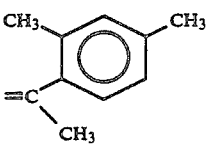 | nD 1.5710 (19.7° C.) | 7.53 |
| 159 | CH$_3$ | CH$_3$ | 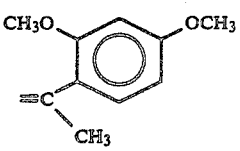 | nD 1.5750 (19.9° C.) | 7.53 |
| 160 | CH$_3$ | CH$_3$ | 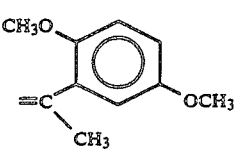 | nD 1.5725 (17.6° C.) | 7.53 |

-continued
| 161 | CH₃ | CH₃ | 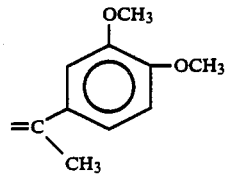 | Green paste | 7.50 |
| 162 | CH₃ | CH₃ | 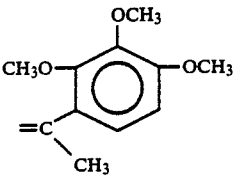 | mp. 102.9–105.5° C. | 7.53 |
| 163 | CH₃ | CH₃ | 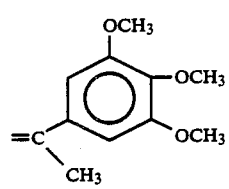 | nD 1.5880 (19.9° C.) | 7.50 |
| 164 | CH₃ | CH₃ | 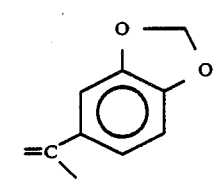 | nD 1.5920 (20.2° C.) | 7.56 |
| 165 | CH₃ | CH₃ | 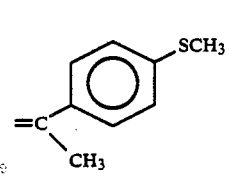 | Yellow paste | 7.53 |
| 166 | CH₃ | CH₃ | 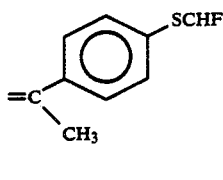 | nD 1.5840 (22.7° C.) | 7.51 |
| 167 | CH₃ | CH₃ | 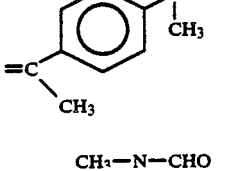 | nD 1.5820 (17.2° C.) | 7.50 |
| 168 | CH₃ | CH₃ | 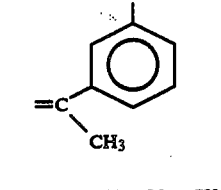 | Colorless paste | 7.50 |
| 169 | CH₃ | CH₃ | 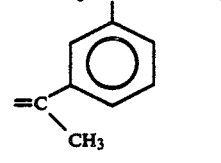 | nD 1.5660 (24.2° C.) | 7.50 |

| | | | | | |
|---|---|---|---|---|---|
| 170 | CH₃ | CH₃ | 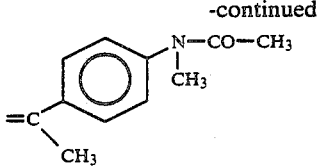 | nD 1.5720 (17.2° C.) | 7.53 |
| 171 | CH₃ | CH₃ | 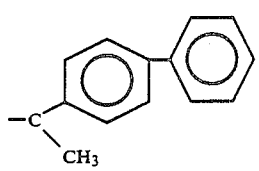 | Green paste | — |
| 172 | CH₃ | CH₃ | 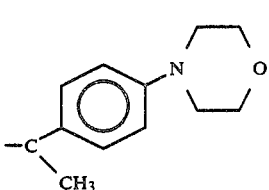 | Colorless paste | 7.56 |
| 173 | CH₃ | CH₃ | 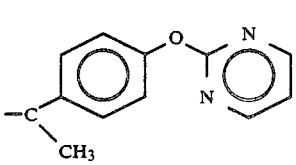 | mp. 169.7–190.8° C. | 7.56 |
| 174 | CH₃ | CH₃ | 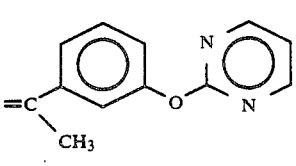 | nD 1.5875 (20.3° C.) | — |
| 175 | CH₃ | CH₃ | 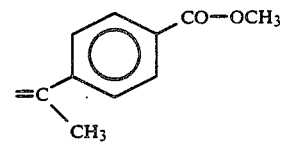 | mp. 84.5–90.9° C. | 7.53 |
| 176 | CH₃ | CH₃ | 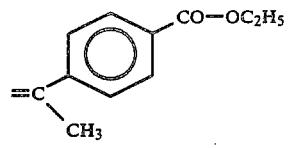 | mp. 114.5–117.4° C. | 7.53 |
| 177 | CH₃ | CH₃ | 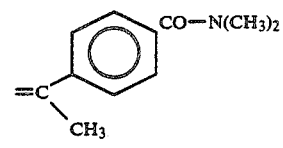 | Yellow paste | 7.53 |
| 178 | CH₃ | CH₃ | 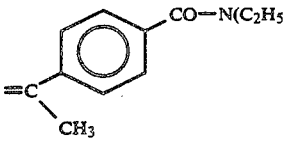 | Colorless paste | 7.50 |
| 179 | CH₃ | CH₃ | 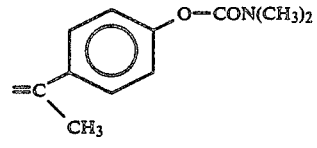 | Colorless paste | 7.53 |

-continued
| | | | | | |
|---|---|---|---|---|---|
| 180 | CH₃ | CH₃ | 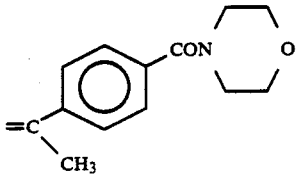 | nD 1.5710 (20.8° C.) | 7.53 |
| 181 | CH₃ | CH₃ | 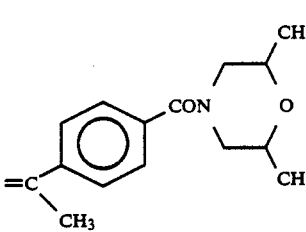 | Yellow paste | 7.53 |
| 182 | CH₃ | CH₃ | 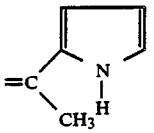 | nD 1.5885 (24.0° C.) | 7.56 |
| 183 | CH₃ | CH₃ | 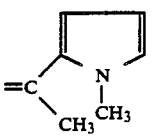 | nD 1.5810 (24.1° C.) | 7.53 |
| 184 | CH₃ | CH₃ | 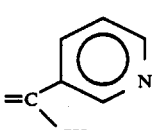 | nD 1.5780 (26.8° C.) | 7.53 |
| 185 | CH₃ | CH₃ | 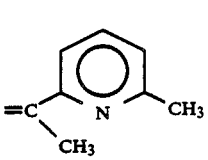 | nD 1.5810 (19.2° C.) | 7.56 |
| 186 | CH₃ | CH₃ | 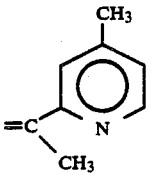 | nD 1.5815 (17.2° C.) | 7.53 |
| 187 | CH₃ | CH₃ | 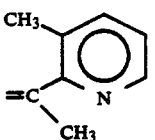 | Colorless paste | 7.50 |
| 188 | CH₃ | CH₃ | 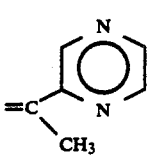 | mp. 100.5–104.3° C. | 7.56 |

-continued
| | | | | | |
|---|---|---|---|---|---|
| 189 | CH₃ | CH₃ | 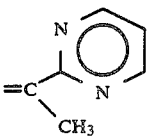 | nD 1.5840 (18.8° C.) | 7.53 |
| 190 | CH₃ | CH₃ | 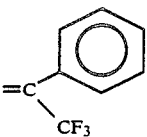 | nD 1.5450 (19.7° C.) | 7.50 |
| 191 | CH₃ | CH₃ | 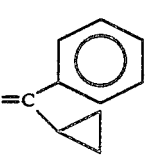 | nD 1.5850 (19.8° C.) | 7.50 |
| 192 | CH₃ | CH₃ | 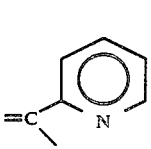 | mp. 81.7–85.0° C. | 7.53 |
| 193 | CH₃ | CH₃ | 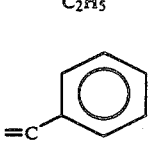 | nD 1.5910 (24.8° C.) | 7.56 |
| 194 | CH₃ | CH₃ | 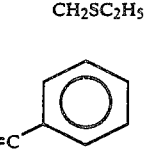 | nD 1.5830 (27.2° C.) | 7.53 |
| 195 | CH₃ | CH₃ | 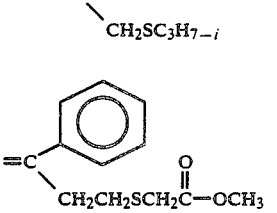 | nD 1.5841 (24.8° C.) | 7.56 |
| 196 | CH₃ | CH₃ | 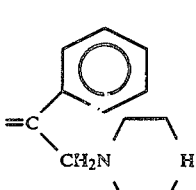 | nD 1.5780 (24.8° C.) | 7.50 |
| 197 | CH₃ | CH₃ | 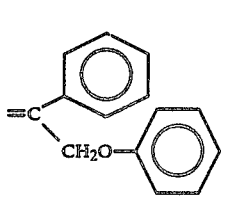 | nD 1.5972 (24.0° C.) | 7.50 |
| 198 | CH₃ | CH₃ | 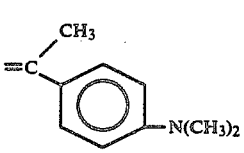 | Colorless paste | 7.50 |

| | | | | | |
|---|---|---|---|---|---|
| 199 | CH$_3$ | CH$_3$ | 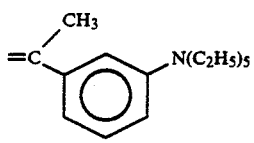 | nD 1.5875 (21.6° C.) | 7.50 |
| 200 | CH$_3$ | CH$_3$ | 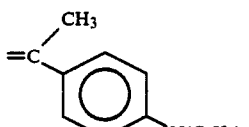 | mp. 95.0–98.8° C. | 7.53 |
| 201 | CH$_3$ | CH$_3$ | 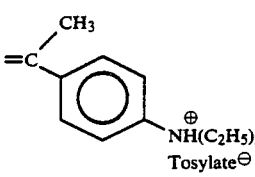 | Colorless paste | — |
| 202 | CH$_3$ | CH$_3$ | 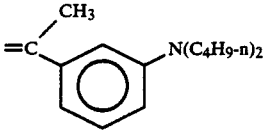 | nD 1.5685 (17.2° C.) | 7.53 |
| 203 | CH$_3$ | CH$_3$ | 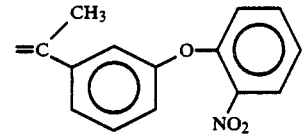 | nD 1.6045 (17.2° C.) | 7.56 |
| 204 | CH$_3$ | CH$_3$ | 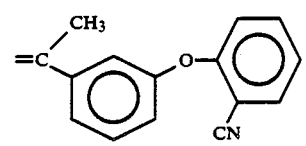 | Colorless paste | — |
| 205 | CH$_3$ | CH$_3$ | 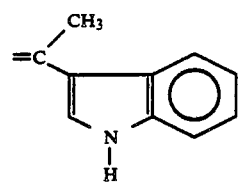 | mp. 169.6° C. | 7.50 |
| 206 | CH$_3$ | CH$_3$ | 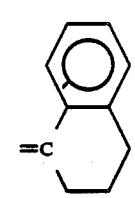 | nD 1.5995 (19.2° C.) | 7.56 |
| 207 | CH$_3$ | CH$_3$ |  | mp. 90.0–96.0° C. | 7.53 |

| | | | | | |
|---|---|---|---|---|---|
| 208 | CH₃ | CH₃ | 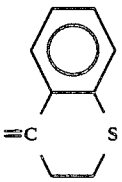 | nD 1.6160 (19.2° C.) | 7.53 |
| 209 | CH₃ | CH₃ | 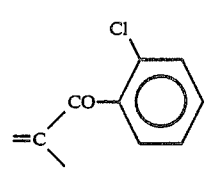 | nD 1.5852 (23.6° C.) | 7.52 |
| 210 | CH₃ | CH₃ | 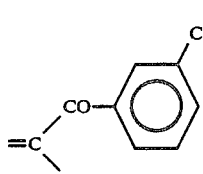 | nD 1.5788 (23.6° C.) (Rf. high) | 7.57 |
| 211 | CH₃ | CH₃ | 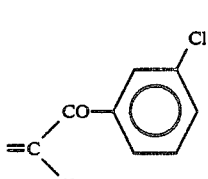 | nD 1.5824 (23.6° C.) (E:Z = 1:1) | 7.57 |
| 212 | CH₃ | CH₃ | 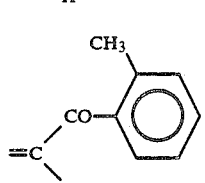 | nD 1.5799 (23.6° C.) | 7.48 |
| 213 | CH₃ | CH₃ | 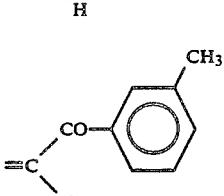 | nD 1.5774 (23.6° C.) (EZ mixture) | 7.54 |
| 214 | CH₃ | CH₃ | 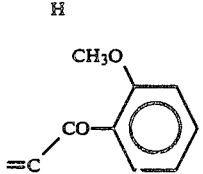 | nD 1.5835 (23.6° C.) | 7.53 |
| 215 | CH₃ | CH₃ | 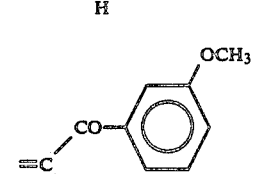 | nD 1.5721 (23.7° C.) (EZ mixture) | 7.48 |
| 216 | CH₃ | CH₃ | 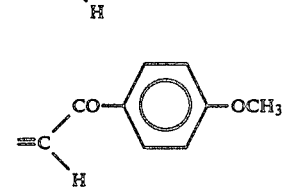 | nD 1.5877 (23.7° C.) (EZ mixture) | 7.56 |

-continued
| | | | | | |
|---|---|---|---|---|---|
| 217 | CH₃ | CH₃ | 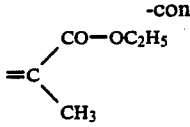 | mp. 70.3–73.6° C. | 7.51 |
| 218 | CH₃ | CH₃ | 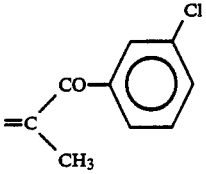 | nD 1.5737 (27.5° C.) (EZ mixture) | 7.54 |
| 219 | CH₃ | CH₃ | 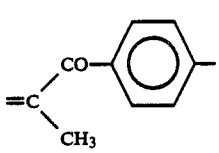 | mp. 80.6–83.5° C. | 7.52 |
| 220 | CH₃ | CH₃ | 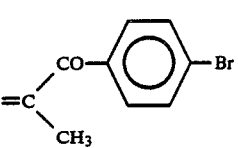 | mp. 89.9–93.0° C. | 7.49 |
| 221 | CH₃ | CH₃ | 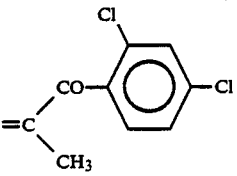 | mp. 120.2–121.4° C. | 7.50 |
| 222 | CH₃ | CH₃ | 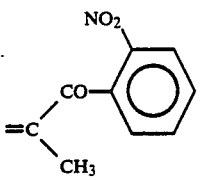 | mp. 97.0–98.8° C. | 7.46 |
| 223 | CH₃ | CH₃ | 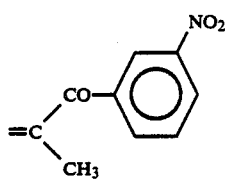 | nD 1.5742 (27.1° C.) (EZ mixture) | 7.53 |
| 224 | CH₃ | CH₃ | 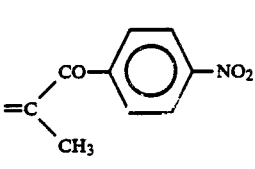 | mp. 86.6–88.3° C. | 7.51 |
| 225 | CH₃ | CH₃ | 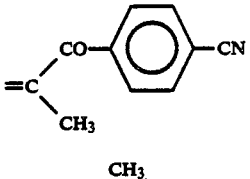 | nD 1.5674 (20.1° C.) | 7.56 |
| 226 | CH₃ | CH₃ | 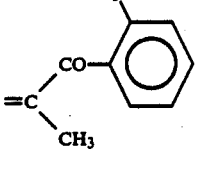 | mp. 82–84° C. | 7.52 |

-continued
| | | | | | |
|---|---|---|---|---|---|
| 227 | CH₃ | CH₃ | 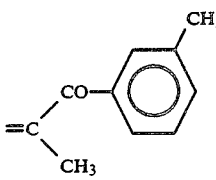 | mp. 80.3–82.1° C. | 7.50 |
| 228 | CH₃ | CH₃ | 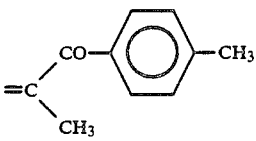 | mp. 90.0–91.5° C. | 7.49 |
| 229 | CH₃ | CH₃ | 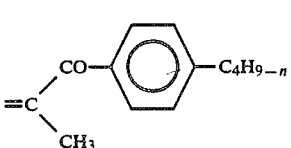 | mp. 69.4–70.7° C. | 7.51 |
| 230 | CH₃ | CH₃ | 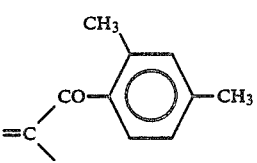 | mp. 92.2–93.8° C. | 7.52 |
| 231 | CH₃ | CH₃ | 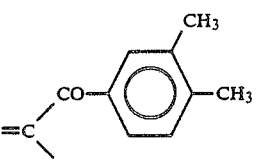 | mp. 81.6–83.1° C. | 7.50 |
| 232 | CH₃ | CH₃ | 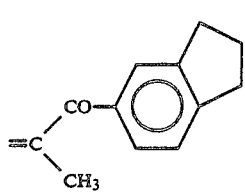 | mp. 87.1–89.6° C. | 7.53 |
| 233 | CH₃ | CH₃ | 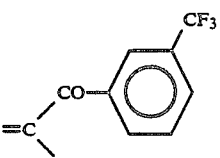 | nD 1.5388 (27.3° C.) | 7.51 |
| 234 | CH₃ | CH₃ | 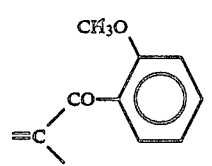 | nD 1.5654 (27.3° C.) | 7.43 |
| 235 | CH₃ | CH₃ | 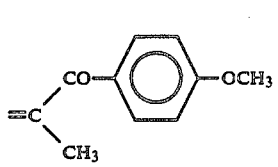 | nD 1.5779 (23.8° C.) | 7.54 |

-continued
| | | | | | |
|---|---|---|---|---|---|
| 236 | CH₃ | CH₃ | 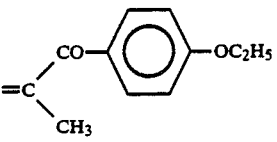 | mp. 98.0–100.6° C. | 7.53 |
| 237 | CH₃ | CH₃ | 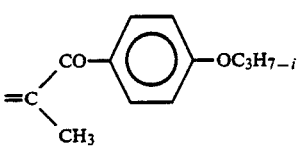 | mp. 110.4–112.6° C. | 7.49 |
| 238 | CH₃ | CH₃ | 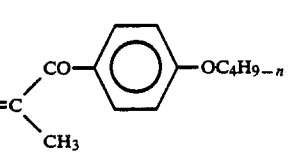 | mp. 79.4–81.3° C. | 7.49 |
| 239 | CH₃ | CH₃ | 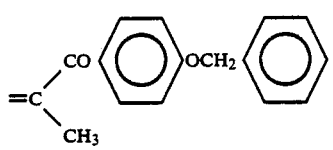 | mp. 85.5–86.9° C. | 7.53 |
| 240 | CH₃ | CH₃ | 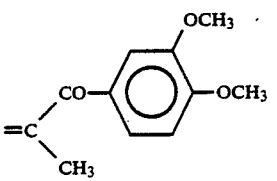 | nD 1.5806 (27.3° C.) (EZ mixture) | 7.51 |
| 241 | CH₃ | CH₃ | 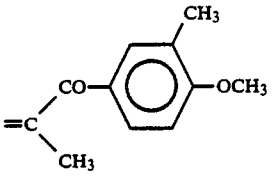 | mp. 72.3–74.8° C. | 7.47 |
| 242 | CH₃ | CH₃ | 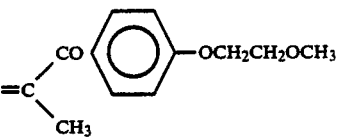 | mp. 79.2–82.2° C. | 7.56 |
| 243 | CH₃ | CH₃ | 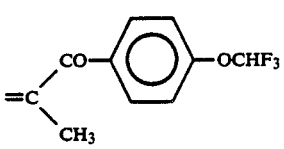 | mp. 60.2–62.0° C. | 7.54 |
| 244 | CH₃ | CH₃ | 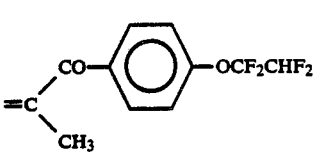 | mp. 65.4–67.5° C. | 7.48 |
| 245 | CH₃ | CH₃ | 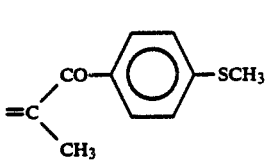 | nD 1.5979 (27.2° C.) (EZ mixture) | 7.51 |

-continued
| | | | | | |
|---|---|---|---|---|---|
| 246 | CH₃ | CH₃ | 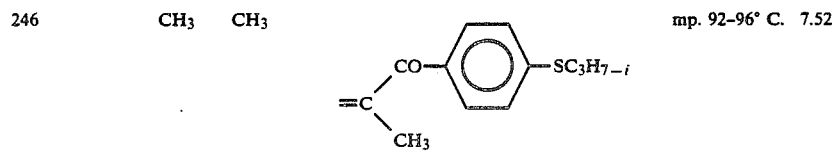 | mp. 92–96° C. | 7.52 |
| 247 | CH₃ | CH₃ | 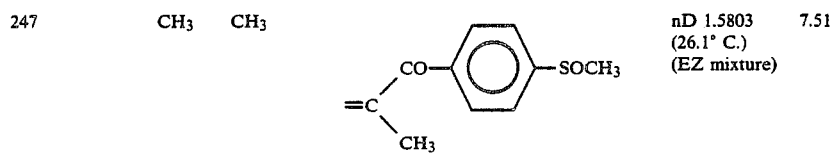 | nD 1.5803 (26.1° C.) (EZ mixture) | 7.51 |
| 248 | CH₃ | CH₃ | 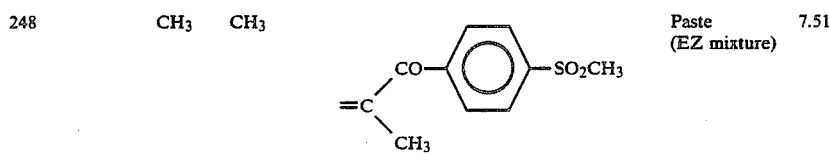 | Paste (EZ mixture) | 7.51 |
| 249 | CH₃ | CH₃ | 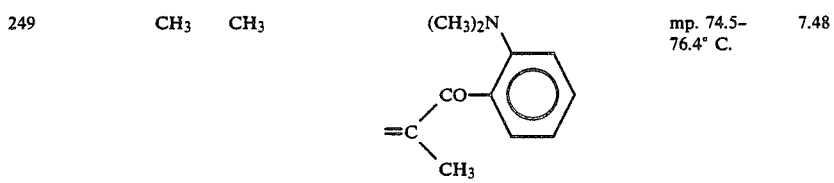 | mp. 74.5–76.4° C. | 7.48 |
| 250 | CH₃ | CH₃ | 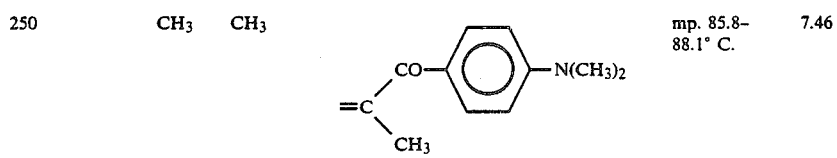 | mp. 85.8–88.1° C. | 7.46 |
| 251 | CH₃ | CH₃ | 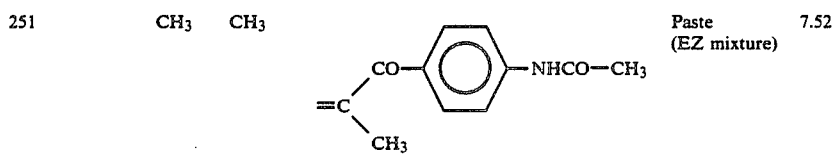 | Paste (EZ mixture) | 7.52 |
| 252 | CH₃ | CH₃ | 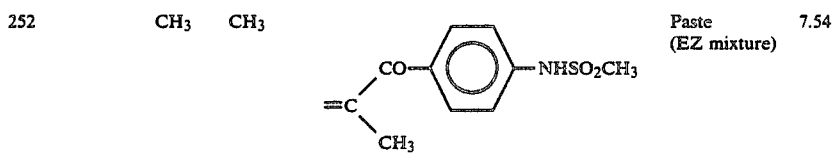 | Paste (EZ mixture) | 7.54 |
| 253 | CH₃ | CH₃ | 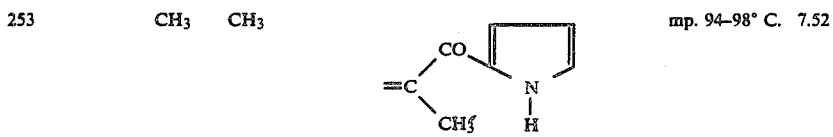 | mp. 94–98° C. | 7.52 |
| 254 | CH₃ | CH₃ | 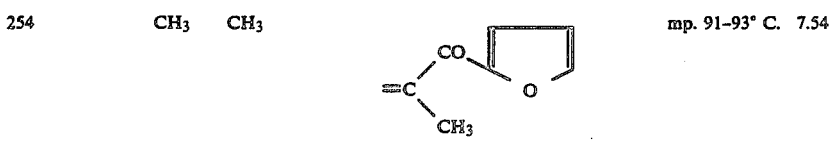 | mp. 91–93° C. | 7.54 |
| 255 | CH₃ | CH₃ | 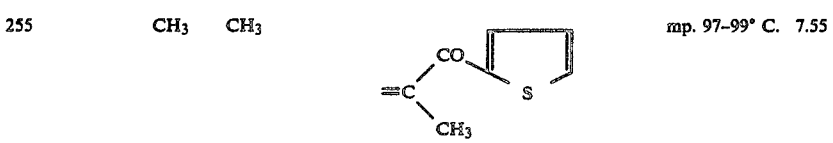 | mp. 97–99° C. | 7.55 |

-continued
| | | | | | |
|---|---|---|---|---|---|
| 256 | CH₃ | CH₃ | 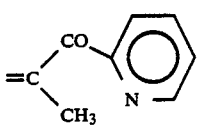 | nD 1.5700 (23.7° C.) | 7.50 |
| 257 | CH₃ | CH₃ | 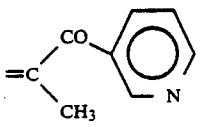 | mp. 121–124° C. | 7.52 |
| 258 | CH₃ | CH₃ | 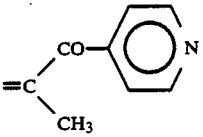 | nD 1.5691 (27.2° C.) | 7.50 |
| 259 | CH₃ | CH₃ | 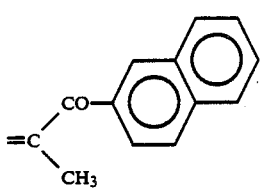 | mp. 106–109° C. | 7.50 |
| 260 | CH₃ | CH₃ | 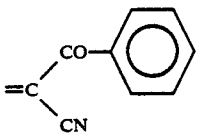 | Amorphous | 7.56 |
| 261 | CH₃ | CH₃ | 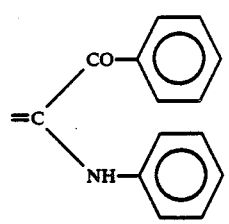 | Amorphous | 7.53 |
| 262 | CH₃ | CH₃ | 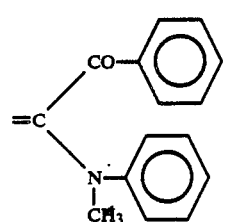 | Amorphous | 7.48 |
| 263 | CH₃ | CH₃ | 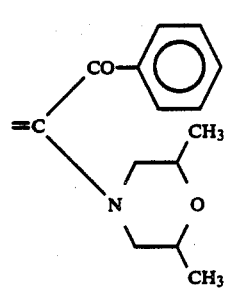 | nD 1.5591 (18.5° C.) | 7.50 |

-continued
| | | | | | |
|---|---|---|---|---|---|
| 264 | CH₃ | CH₃ | 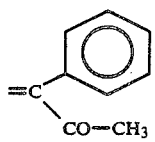 | Amorphous | 7.50 |
| 265 | CH₃ | CH₃ | 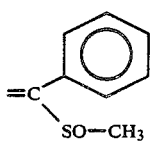 | nD 1.5879 (20.0° C.) | 7.50 |
| 266 | CH₃ | CH₃ | 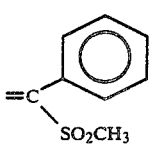 | nD 1.5692 (20.0° C.) | 7.56 |
| 267 | CH₃ | CH₃ | 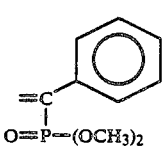 | mp. 117–119° C. | 7.53 |
| 268 | CH₃ | CH₃ | 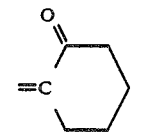 | nD 1.5692 (20.0° C.) | 7.50 |
| 269 | CH₃ | CH₃ | 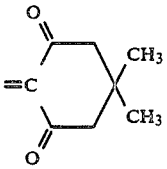 | nD 1.5502 (20.2° C.) | 7.50 |
| 270 | CH₃ | CH₃ | 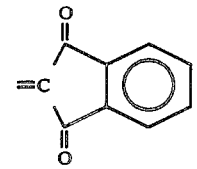 | mp. 196–199° C. | 7.63 |
| 271 | CH₃ | CH₃ | 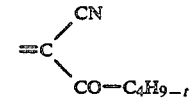 | nD 1.5265 (22.6° C.) | 7.63 |
| 272 | CH₃ | CH₃ | 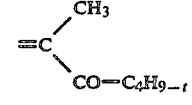 | mp. 55–56 C. | 7.60 |
| 273 | CH₃ | CH₃ | 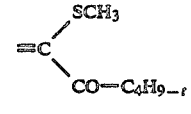 | nD 1.5460 (23.2° C.) | 7.60 |
| 274 | CH₃ | CH₃ | 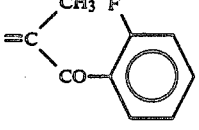 | nD 1.5690 (23.4° C.) | 7.54 |

-continued

| | | | | | |
|---|---|---|---|---|---|
| 275 | CH₃ | CH₃ | =C(CH₃)-CO-O-(3-Br-C₆H₄) | nD 1.5925 (23.4° C.) | 7.58 |
| 276 | CH₃ | CH₃ | =C(CH₃)-CO-O-(3-NC-C₆H₄) | nD 1.5767 (23.6° C.) | 7.59 |
| 277 | CH₃ | CH₃ | =C(CH₃)-CO-O-(4-n-C₃H₇-C₆H₄) | nD 1.5703 (23.3° C.) | 7.58 |
| 278 | CH₃ | CH₃ | =C(CH₃)-CO-O-(4-t-C₄H₉-C₆H₄) | nD 1.5576 (23.4° C.) | 7.59 |
| 279 | CH₃ | CH₃ | =C(CH₃)-CO-O-(4-C₆H₅-C₆H₄) | nD 1.5964 (23.3° C.) | 7.58 |
| 280 | CH₃ | CH₃ | =C(CH₃)-CO-O-(4-C₆H₅CH₂-C₆H₄) | mp. 87.0–90.4° C. | 7.56 |
| 281 | CH₃ | CH₃ | =C(CH₃)-CO-O-(2-CF₃-C₆H₄) | nD 1.5386 (23.3° C.) | 7.53 |
| 282 | CH₃ | CH₃ | =C(CH₃)-CO-O-(4-CF₃-C₆H₄) | nD 1.5338 (23.4° C.) | 7.57 |
| 283 | CH₃ | CH₃ | =C(CH₃)-CO-O-(3-OCH₃-C₆H₄) | nD 1.5702 (21.5° C.) | 7.57 |
| 284 | CH₃ | CH₃ | =C(CH₃)-CO-O-(3-i-OC₃H₇-C₆H₄) | nD 1.5502 (21.5° C.) | 7.57 |
| 285 | CH₃ | CH₃ | =C(CH₃)-CO-O-(3-OCHF₂-C₆H₄) | nD 1.5511 (21.5° C.) | 7.57 |

| No. | R1 | R2 | Structure | Properties | Value |
|---|---|---|---|---|---|
| 286 | CH₃ | CH₃ | =C(CH₃)-CO-O-C₆H₄-OCF₂CHF₂ | nD 1.5294 (21.5° C.) | 7.57 |
| 287 | CH₃ | CH₃ | =C(CH₃)-CO-O-C₆H₄-O-C₆H₅ (para) | nD 1.5892 (22.5° C.) | 7.56 |
| 288 | CH₃ | CH₃ | =C(CH₃)-CO-O-C₆H₄-O-C₆H₅ (meta) | nD 1.5878 (22.5° C.) | 7.53 |
| 289 | CH₃ | CH₃ | =C(CH₃)-CO-O-C₆H₄-O-C₆H₄-CN (o) | nD 1.5750 (22.5° C.) | 7.56 |
| 290 | CH₃ | CH₃ | =C(CH₃)-CO-O-C₆H₄-O-C₆H₄-NO₂ (o) | nD 1.5750 (22.5° C.) | 7.53 |
| 291 | CH₃ | CH₃ | =C(CH₃)-CO-O-C₆H₄-O-(2-pyridyl) | Amorphous | 7.57 |
| 292 | CH₃ | CH₃ | =C(C₃H₇-n)(SCH₃) | nD 1.5900 (26.1° C.) | 7.56 |
| 293 | CH₃ | CH₃ | =C(C₃H₇-i)(SCH₃) | nD 1.5555 (26.6° C.) | 7.57 |
| 294 | CH₃ | CH₃ | =C(C₅H₁₁-n)(SCH₃) | nD 1.5410 (27.8° C.) | 7.54 |
| 295 | CH₃ | CH₃ | =C(C₆H₁₃-n)(SCH₃) | nD 1.5440 (26.3° C.) | 7.56 |
| 296 | CH₃ | CH₃ | =C(C₇H₁₅-n)(SCH₃) | nD 1.5311 (28.0° C.) | 7.54 |

-continued

| | | | | | |
|---|---|---|---|---|---|
| 297 | CH₃ | CH₃ | =C(C₉H₁₉-n)(SCH₃) | nD 1.5299 (27.8° C.) | 7.54 |
| 298 | CH₃ | CH₃ | =C(SCH₃)−CH(C₂H₅)(C₆H₁₃-n) | nD 1.5361 (28.2° C.) | 7.54 |
| 299 | CH₃ | CH₃ | =C(SCH₃)−CO−O−C₆H₅ | nD 1.5572 (25.7° C.) | 7.56 |
| 300 | CH₃ | CH₃ | =C(SCH₃)−C₆H₄−Br | mp. 119–121° C. | 7.57 |
| 301 | CH₃ | CH₃ | =C(SCH₃)−C₆H₃(Cl)(Cl) | nD 1.5909 (26.8° C.) | 7.57 |
| 302 | CH₃ | CH₃ | =C(SCH₃)−CH(CH₃)−C₆H₅ | nD 1.5760 (28.0° C.) | 7.61 |
| 303 | CH₃ | CH₃ | =C(SCH₃)−C₆H₁₀−H | nD 1.5576 (28.4° C.) | 7.54 |
| 304 | CH₃ | CH₃ | =C(SCH₃)−C₆H₄−O−C₆H₄−CN | Paste | 7.61 |
| 305 | CH₃ | CH₃ | =C(NH₂)−C₆H₄−CN | Paste | 7.59 |
| 306 | CH₃ | CH₃ | =C(NH₂)−C₆H₄−NO₂ | Paste | 7.57 |

-continued

| No. | | | Structure | Form | Value |
|---|---|---|---|---|---|
| 307 | CH₃ | CH₃ | =C(NH₂)(4-Cl-C₆H₄) | Paste | 7.51 |
| 308 | CH₃ | CH₃ | =C(NH₂)(4-F-C₆H₄) | Paste | 7.51 |
| 309 | CH₃ | CH₃ | =C(NH₂)(4-Br-C₆H₄) | Paste | 7.52 |
| 310 | CH₃ | CH₃ | =C(NH₂)(4-CF₃-C₆H₄) | Paste | 7.55 |
| 311 | CH₃ | CH₃ | =C(NH₂)(3-(2-CN-C₆H₄-O)-C₆H₄) | Paste | 7.58 |
| 312 | CH₃ | CH₃ | =C(NHCH₃)(C₆H₁₃-n) | nD 1.5308 (24.8° C.) | 7.54 |
| 313 | CH₃ | CH₃ | =C(NHCH₃)(CH(C₂H₅)(C₅H₁₁-n)) | nD 1.5292 (24.3° C.) | 7.52 |
| 314 | CH₃ | CH₃ | =C(NHCH₃)(4-CF₃-C₆H₄) | nD 1.5451 (21.9° C.) | 7.55 |
| 315 | CH₃ | CH₃ | =C(NHCH₃)(4-Br-C₆H₄) | nD 1.5885 (22.0° C.) | 7.53 |
| 316 | CH₃ | CH₃ | =C(NHCH₃)(4-OCH₃-C₆H₄) | nD 1.5805 (21.7° C.) | 7.55 |
| 317 | CH₃ | CH₃ | =C(NHCH₃)(OCH₃)(C₆H₅-CH₂) | Paste | 7.53 |

-continued

| | | | | | |
|---|---|---|---|---|---|
| 318 | CH₃ | CH₃ | =C(NHCH₃)-C₆H₃(NO₂) (para-NO₂) | nD 1.5922 (22.8° C.) | 7.55 |
| 319 | CH₃ | CH₃ | =C(NHCH₃)-C₆H₃(CN) (meta-CN) | nD 1.5832 (22.6° C.) | 7.54 |
| 320 | CH₃ | CH₃ | =C(NHCH₃)-C₆H₃(CF₃) (ortho-CF₃) | nD 1.5475 (22.7° C.) | 7.54 |
| 321 | CH₃ | CH₃ | =C(NHCH₃)-C₆H₃(NO₂) (meta-NO₂) | nD 1.5805 (22.2° C.) | 7.56 |
| 322 | CH₃ | CH₃ | =C(NHCH₃)-C₆H₄-O-C₆H₄(CN) | Paste | 7.60 |
| 323 | CH₃ | CH₃ | =C(NHCH₃)-CH₂CH₂-C₆H₅ | nD 1.5671 (21.0° C.) | 7.56 |
| 324 | CH₃ | CH₃ | =C(CH₃)-NH(CH₂)₃N(morpholine) | nD 1.5409 (20.5° C.) | 7.52 |
| 325 | CH₃ | CH₃ | =C(CH₃)-NH(CH₂)₂N(morpholine) | nD 1.5435 (21.2° C.) | 7.53 |
| 326 | CH₃ | CH₃ | =C(CH₃)-NH(CH₂)₂-(2-pyridyl) | nD 1.5568 (21.2° C.) | 7.52 |
| 327 | CH₃ | CH₃ | =C(NH(CH₂)₂OCH₃)-C₆H₃(CF₃) (para-CF₃) | Paste | 7.61 |

-continued

| | | | | | |
|---|---|---|---|---|---|
| 328 | CH₃ | CH₃ | =C with phenyl (4-CF₃) and NH(CH₂)₂N(CH₃)₂ | Paste | 7.61 |
| 329 | CH₃ | CH₃ | =C with phenyl and NH₂ | nD 1.5975 (23.0° C.) | 7.54 |
| 330 | CH₃ | CH₃ | =C with phenyl (3-OPh) and NH₃ | Paste | 7.49 |
| 331 | CH₃ | CH₃ | =C with phenyl and NHCH₂CH=CH₂ | nD 1.5797 (24.8° C.) | 7.56 |
| 332 | CH₃ | CH₃ | =C with phenyl (3-OPh) and NHCH₃ | Paste | 7.56 |
| 333 | CH₃ | CH₃ | =C with phenyl (3-OPh) and NHC₂H₅ | nD 1.5888 (24.7° C.) | 7.54 |
| 334 | CH₃ | CH₃ | =C with phenyl (4-CF₃) and NHCH₂CH=CH₂ | nD 1.5483 (18.7° C.) | 7.58 |
| 335 | CH₃ | CH₃ | =C with phenyl (4-CF₃) and NHCH₂C≡CH | nD 1.5498 (19.9° C.) | 7.62 |
| 336 | CH₃ | CH₃ | =C with phenyl (4-CF₃) and NHCH₂CF₃ | Paste | 7.61 |
| 337 | CH₃ | CH₃ | =C with phenyl (4-CF₃) and NHCH₂CH(OCH₃)₂ | nD 1.5418 (21.7° C.) | 7.60 |

-continued

| No. | R1 | R2 | Group | Property | Value |
|---|---|---|---|---|---|
| 338 | CH₃ | CH₃ | =C(OCH₃)(C₆H₅) | nD 1.5735 (21.0° C.) (EZ mixture) | 7.53 & 7.57 |
| 339 | CH₃ | CH₃ | =C(OCH₃)(C₆H₅) | nD 1.5802 (19.7° C.) (E or Z) | 7.57 |
| 340 | CH₃ | CH₃ | =C(OC₂H₅)(C₆H₅) | nD 1.5756 (22.1° C.) | 7.60 |
| 341 | CH₃ | CH₃ | =C(OCH₃)(4-Cl-C₆H₄) | nD 1.5861 (22.7° C.) | 7.59 |
| 342 | CH₃ | CH₃ | =C(OCH₃)(3-phenoxyphenyl) | nD 1.5973 (23.1° C.) | 7.59 |
| 343 | CH₃ | CH₃ | =C(CH₃)(pyrrolidin-1-yl) | nD 1.5531 (27.6° C.) | 7.54 |
| 344 | CH₃ | CH₃ | =C(CH₃)(1,2,4-triazol-1-yl) | mp. 74–76° C. | 7.55 |
| 345 | CH₃ | CH₃ | =C(CH₃)(piperidin-1-yl) | nD 1.5323 (25.1° C.) | 7.53 |
| 346 | CH₃ | CH₃ | =C(CH₃)(2-methylpiperidin-1-yl) | nD 1.5442 (20.2° C.) | 7.53 |

| | | | | | |
|---|---|---|---|---|---|
| 347 | CH₃ | CH₃ | 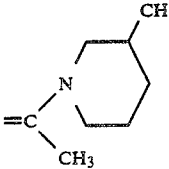 | nD 1.5389 (20.5° C.) | 7.53 |
| 348 | CH₃ | CH₃ | 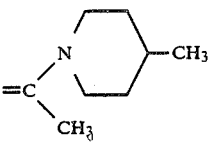 | nD 1.5409 (25.3° C.) | 7.55 |
| 349 | CH₃ | CH₃ | 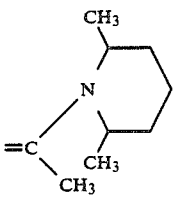 | nD 1.5392 (22.8° C.) | 7.56 |
| 350 | CH₃ | CH₃ | 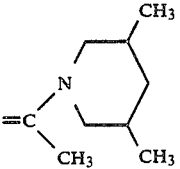 | nD 1.5350 (22.8° C.) | 7.53 |
| 351 | CH₃ | CH₃ | 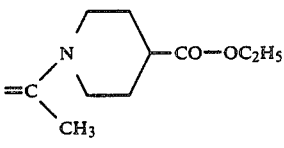 | nD 1.5400 (19.4° C.) | 7.53 |
| 352 | CH₃ | CH₃ | 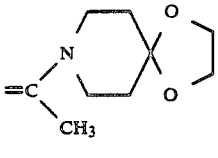 | nD 1.5520 (26.8° C.) | 7.51 |
| 353 | CH₃ | CH₃ | 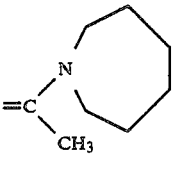 | nD 1.5580 (24.3° C.) | 7.55 |
| 354 | CH₃ | CH₃ | 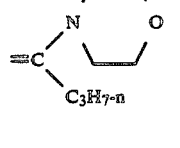 | nD 1.5119 (21.7° C.) | 7.53 |
| 355 | CH₃ | CH₃ | 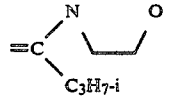 | nD 1.5330 (22.1° C.) | 7.54 |

-continued
| | | | | | |
|---|---|---|---|---|---|
| 356 | CH₃ | CH₃ | 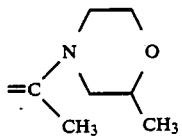 | mp. 82.2–83.9° C. | 7.55 |
| 357 | CH₃ | CH₃ | 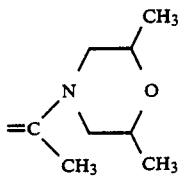 | mp. 107–109° C. (cis-form) | 7.54 |
| 358 | CH₃ | CH₃ | 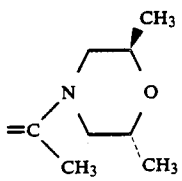 | nD 1.5374 (17.8° C.) (trans-form) | 7.55 |
| 359 | CH₃ | CH₃ | 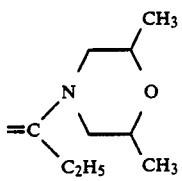 | nD 1.5360 (12.9° C.) (cis-form) | 7.53 |
| 360 | CH₃ | CH₃ | 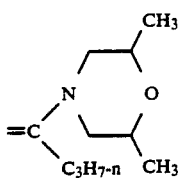 | nD 1.5205 (23.8° C.) (cis-form) | 7.53 |
| 361 | CH₃ | CH₃ | 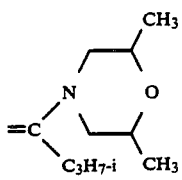 | nD 1.5121 (24.4° C.) (cis-form) | 7.57 |
| 362 | CH₃ | CH₃ | 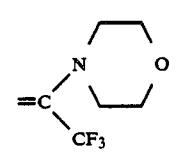 | nD 1.5203 (23.7° C.) | 7.58 |
| 363 | CH₃ | CH₃ | 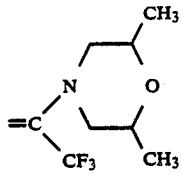 | nD 1.5088 (21.4° C.) (cis-form) | 7.55 |
| 364 | CH₃ | CH₃ | 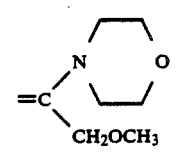 | nD 1.5431 (27.0° C.) | 7.55 |

| | | | | | |
|---|---|---|---|---|---|
| 365 | CH₃ | CH₃ | (morpholine ring with CH₃ groups, =C-CH₂OCH₃) | nD 1.5221 (27.2° C.) (cis-form) | 7.57 |
| 366 | CH₃ | CH₃ | (thiomorpholine, =C-CH₃) | nD 1.5675 (25.0° C.) | 7.54 |
| 367 | CH₃ | CH₃ | (N-methylpiperazine, =C-CH₃) | nD 1.5456 (18.2° C.) | 7.53 |
| 368 | CH₃ | CH₃ | (N-phenylpiperazine, =C-CH₃) | nD 1.5840 (18.0° C.) | 7.57 |
| 369 | CH₃ | CH₃ | (N-benzylpiperazine, =C-CH₃) | nD 1.5612 (25.0° C.) | 7.54 |
| 370 | CH₃ | CH₃ | (1,2,3,4-tetrahydroquinoline, =C-CH₃) | nD 1.5906 (17.6° C.) | 7.59 |
| 371 | CH₃ | CH₃ | (1,2,3,4-tetrahydroisoquinoline, =C-CH₃) | mp. 124.3–127.2° C. | 7.57 |
| 372 | CH₃ | CH₃ | (benzomorpholine, =C-CH₃) | nD 1.5898 (23.3° C.) | 7.59 |
| 373 | C₂H₅ | CH₃ | (N-phenyl, =C-CH₃) | nD 1.5852 (26.5° C.) | 7.61 |

-continued
| | | | | | |
|---|---|---|---|---|---|
| 374 | CH₃ | C₂H₅ | 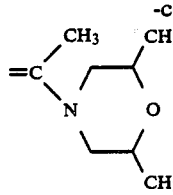 | mp. 96.3–97.2° C. (cis-form) | 7.54 |
| 375 | CH₃ | CH₃ | 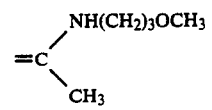 | nD 1.5359 (26.1° C.) | 7.49 |
| 376 | CH₃ | CH₃ | 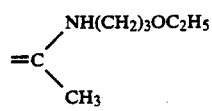 | nD 1.5277 (25.9° C.) | 7.51 |
| 377 | CH₃ | CH₃ | 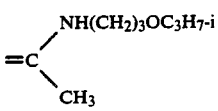 | nD 1.5203 (26.0° C.) | 7.50 |
| 378 | CH₃ | CH₃ | 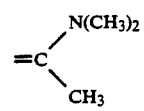 | | |
| 379 | CH₃ | CH₃ | 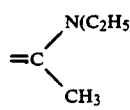 | nD 1.5382 (22.4° C.) | 7.48 |
| 380 | CH₃ | CH₃ | 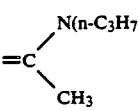 | nD 1.5271 (22.6° C.) | 7.47 |
| 381 | CH₃ | CH₃ | 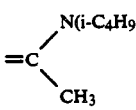 | nD 1.5157 (23.0° C.) | 7.48 |
| 382 | CH₃ | CH₃ | 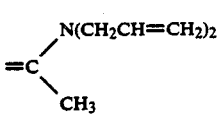 | nD 1.5419 (24.2° C.) | 7.51 |
| 383 | CH₃ | CH₃ | 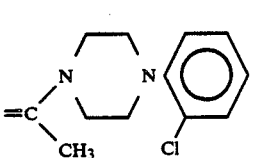 | Pale yellow paste | 7.51 |
| 384 | CH₃ | CH₃ | 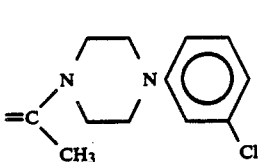 | Pale yellow paste | 7.54 |
| 385 | CH₃ | CH₃ | 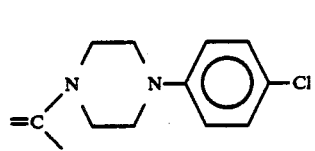 | Pale brown paste | 7.52 |

| | | | | | |
|---|---|---|---|---|---|
| 386 | CH₃ | CH₃ | 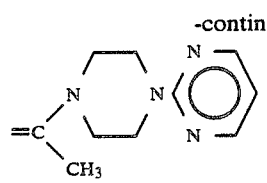 | Pale yellow paste | 7.53 |
| 387 | CH₃ | CH₃ | 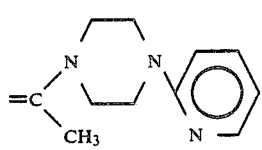 | nD 1.5869 (24.2° C.) | 7.57 |
| 388 | CH₃ | CH₃ | 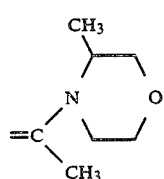 | mp. 92.2– 95.3° C. | 7.52 |
| 389 | CH₃ | CH₃ | 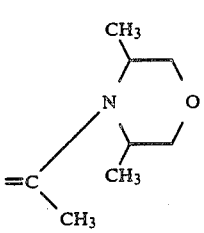 | mp. 126.0 128.3° C. (cis-form) | 7.56 |
| 390 | CH₃ | CH₃ | 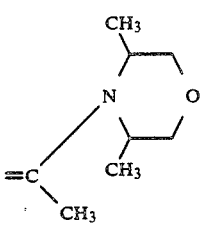 | nD 1.5327 (21.3° C.) (trans-form) | 7.55 |
| 391 | CH₃ | CH₃ | 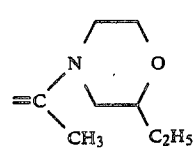 | mp. 90.2– 92.7° C. | 7.55 |
| 392 | CH₃ | CH₃ | 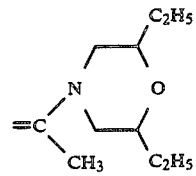 | nD 1.5342 (23.1° C.) (cis-form) | 7.55 |
| 393 | CH₃ | CH₃ | 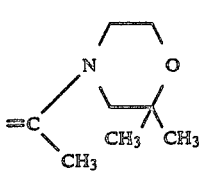 | nD 1.5446 (23.1° C.) | 7.55 |
| 394 | CH₃ | CH₃ | 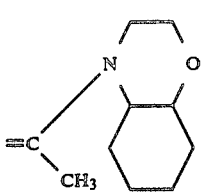 | nD 1.5386 (23.2° C.) | 7.53 |

| No. | R1 | R2 | Group | Physical data | NMR |
|---|---|---|---|---|---|
| 395 | CH₃ | CH₃ | =C(CH₃)-N(morpholine with 3,5-diCH₃) | nD 1.5371 (25.0° C.) | 7.53 |
| 396 | CH₃ | CH₃ | =C(CH₃)-CO-OC₄H₉-t | mp. 96.6–100.3° C. | 7.50 |
| 397 | CH₃ | CH₃ | =C(CH₃)-CO-SC₃H₇-i | nD 1.5520 (25.5° C.) | 7.58 |
| 398 | CH₃ | CH₃ | =C(CH₃)-CO-N(C₃H₇-n)₂ | nD 1.5254 (26.0° C.) (EZ mixture) | 7.56 & 7.48 |
| 399 | CH₃ | CH₃ | =C(CH₃)-CO-NH-C₆H₅ | ND 1.5809 (26.0° C.) | 7.68 |
| 400 | CH₃ | CH₃ | =C(CH₃)-CO-N(CH₃)-C₆H₅ | nD 1.5591 (26.0° C.) (EZ mixture) | 7.56 & 7.51 |
| 401 | CH₃ | CH₃ | =C(CH₃)-CO-OCH₂-C₆H₄-OCH₃ | nD 1.5459 (25.5° C.) | 7.55 |
| 402 | CH₃ | CH₃ | =C(CH₃)-CO-O-(3,4-methylenedioxyphenyl) | nD 1.5790 (26.0° C.) | 7.50 |
| 403 | CH₃ | CH₃ | =C(CH₃)-CO-N(morpholine with 3,5-diCH₃) | nD 1.5388 (26.0° C.) | 7.56 |
| 404 | C₂H₅ | CH₃ | =C(CH₃)-C₆H₅ | nD 1.5388 (26.0° C.) | 7.56 |

| | | | | | |
|---|---|---|---|---|---|
| 405 | CH₃ | C₂H₅ | 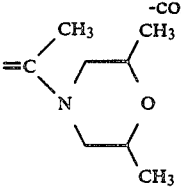 | mp. 96.3–97.2° C. (cis-form) | 7.54 |
| 406 | CH₃ | i-C₃H₇ | 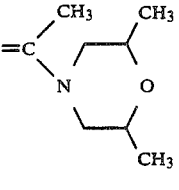 | Paste (cis-form) | 7.47 |
| 407 | C₂H₅ | CH₃ | 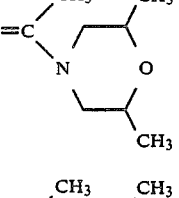 | nD 1.5421 (26.7° C.) | 7.47 |
| 408 | i-C₃H₇ | CH₃ | 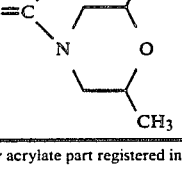 | nD 1.5281 (29.3° C.) | 7.66 |

*¹H-NMR chemical shift of olefinic protones of methoxy acrylate part registered in deutero chloroform with tetramethylsilane as an internal standard [δ value (ppm)].

In compounds described in Table 1, a combination, e.g. of compounds 55 and 56, compounds 57 and 58, or the like is a combination of an isomer having a Z form with an isomer having a E form.

Further, in Table 1, the terms of "high" and "low" Rf mean a high Rf value and a low Rf value in silica gel thin layer chromatography (n-hexane-ethyl acetate).

The following Examples illustrate typical embodiments of the N-(substituted benzyloxy)imine derivative of the general formula (I), to which, however, this invention shall not be limited.

EXAMPLE 1

Methyl 2-(2-benzylideneaminooxymethylphenyl)-3-methoxyacrylate (Compound No. 1)

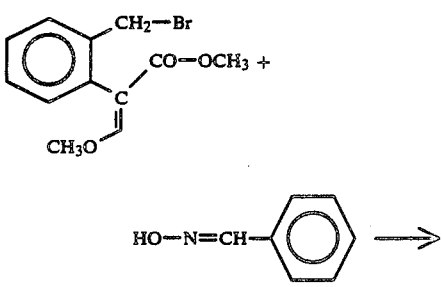

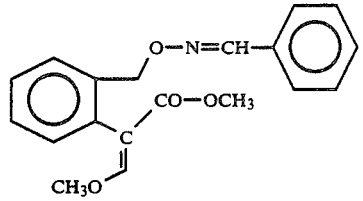

0.57 Gram of methyl 2-(2-bromomethylphenyl)-3-methoxyacrylate and 0.36 g of benzaldoxime were dissolved in 10 ml of dimethyl sulfoxide, and 0.19 g of potassium hydroxide powder was added. The resultant mixture was stirred at room temperature for 6 hours.

After standing overnight, the mixture was poured into ice water, to wash with brine, and extracted twice with ethyl acetate. The extracts were dried over magnesium sulfate, filtered and concentrated under reduced pressure, and the resultant residue was purified by silica gel dry column chromatography to give 0.2 g of the intended product.

Yield: 31%, Properties: nD 1.5905 (18.9° C.)

EXAMPLE 2

Methyl 2-{2-(3-oxo-2-butylideneaminooxymethyl)-phenyl}-3-methoxyacrylate (Compound No. 52)

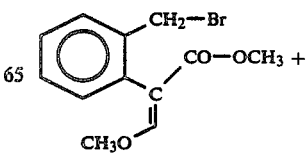

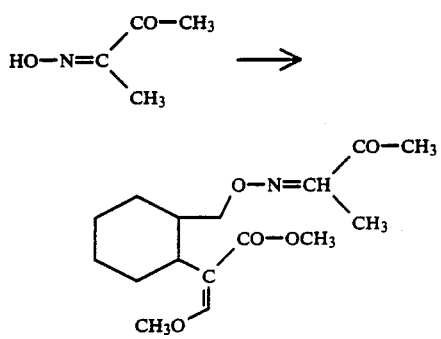

0.86 Gram of methyl 2-(2-bromomethylphenyl)-3-methoxyacrylate and 0.33 g of diacetyl monooxime were dissolved in 20 ml of dimethylformamide, and the mixture was cooled to 5° C. 0.22 Gram of potassium hydroxide powder was added, and the mixture was stirred for 10 minutes and further stirred for 1 hour at room temperature to carry out the reaction. After completion of the reaction, the reaction mixture was poured into ice water, and extracted with ethyl acetate. The extracts were washed with a 5% sodium hydroxide aqueous solution and salt water, and dried over magnesium sulfate. The extracts were filtered and concentrated under reduced pressure, and the resultant residue was purified by silca gel dry column chromatography to give 0.81 g of the intended product.

Yield: 89%, Properties: mp. 82.7°-84.6° C.

EXAMPLE 3

Methyl 2-{2-(α-methylthiobenzylideneaminooxymethyl)phenyl}-3-methoxyacrylate (Compound No. 59)

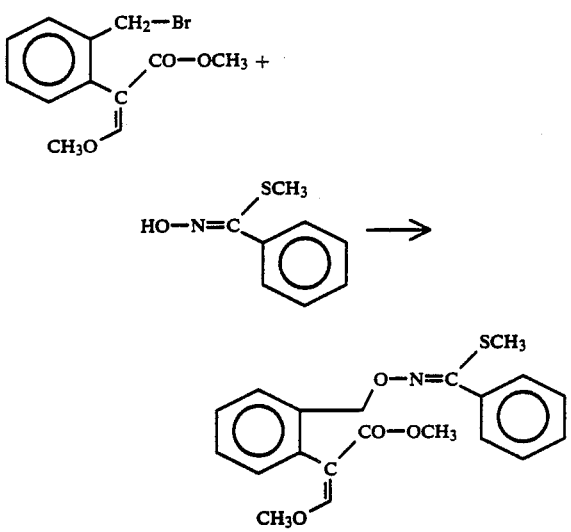

0.33 Gram of potassium hydroxide powder was added to 10 ml of a dimethyl sulfoxide solution containing 0.85 g of benzhydroxamyl methyl thioether, and the mixture was stirred for 10 minutes. Then, 1.45 g of methyl 2-(2-bromomethylphenyl)-3-methoxyacrylate was added, and the resultant mixture was allowed to react with stirring for 4 hours.

After completion of the reaction, the reaction mixture was poured into ice water and extracted with ether. The extracts were washed with water and brine, and dried over sodium sulfate. The extract liquid was filtered and then concentrated under reduced pressure, and the resultant residue was purified by silica gel dry column chromatography to give 1.50 g of the intended product.

Yield: 81%, Properties: nD 1.5924 (18.6° C.).

Methyl 2-{2-(α-morpholinobenzylideneaminooxymethyl)phenyl}-3-methoxyacrylate (Compound No. 88)

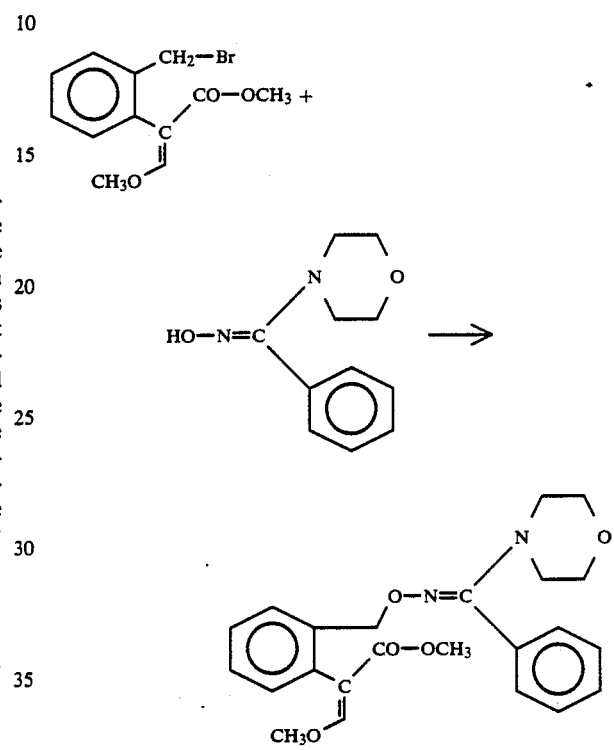

0.44 Gram of α-morpholinobenzaldoxime was dissolved in 5 ml of dimethyl sulfoxide, and 0.14 g of potassium hydroxide powder was added. The mixture was stirred for 30 minutes. Then, 0.55 g of methyl 2-(2-bromomethylphenyl)-3-methoxyacrylate was added, and the mixture was allowed to react with stirring for 2 hours.

After the completion of the reaction, 10 ml of ice water was added to the reaction mixture, and the resultant was extracted with ethyl acetate. The extracts were washed with water, and dried over sodium sulfate. The extracts were filtered and concentrated under reduced pressure, and the resultant residue was purified by silica gel dry column chromatography to give 0.29 g of the intended product.

Yield: 33%, Properties: paste.

EXAMPLE 5

Methyl 2-{2-(1,3-dithiolan-2-ylideneaminooxymethyl)phenyl}-3-methoxyacrylate (Compound No. 96)

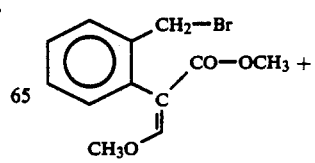

-continued

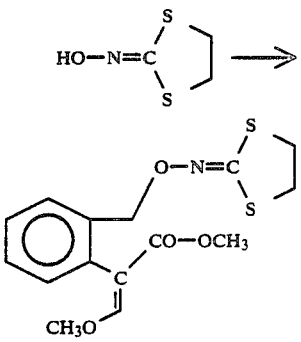

0.44 Gram of 2-hydroxyimino-1,3-dithiolane was dissolved in 5 ml of dimethyl sulfoxide, and 0.18 g of potassium hydroxide powder was added. The resultant mixture was stirred at room temperature for 30 minutes. Then, 0.86 g of methyl 2-(2-bromomethylphenyl)-3-methoxyacrylate was added, and the resultant mixture was allowed to react with stirring for 2 hours.

After completion of the reaction, ice water was added to the reaction mixture which was extracted with ethyl acetate. The extracts were washed with water, and dried over magnesium sulfate. The extracts were filtered and concentrated under reduced pressure, and the resultant residue was purified by silica gel dry column chromatography to give 0.56 g of the intended product.

Yield: 55%, Properties: nD 1.5917 (18.6° C.).

EXAMPLE 6

Methyl 2-[2-{1-(cis-2,6-dimethylmorpholino)ethylideneaminooxymethylphenyl]-3-methoxyacrylate (Compound No. 357)

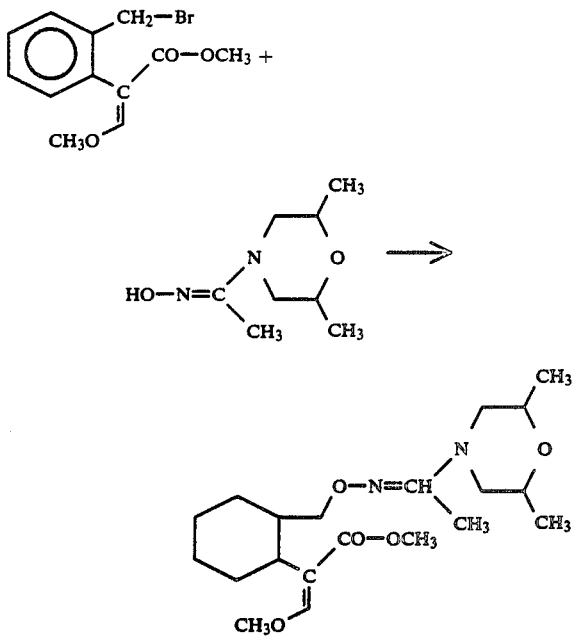

1.72 Gram of 1-(cis-2,6-dimethylmorpholino)acetoaldoxime was dissolved in 30 ml of dimethylformamide, and 0.66 g of potassium hydroxide powder was added thereto, and the mixture was stirred for 10 minutes at 0° C. 2.85 Grams of methyl 2-(2-bromomethylphenyl)-3-methoxyacrylate was added thereto and the resultant mixture was further stirred for 1 hour at room temperature to carry out the reaction. After completion of the reaction, the reaction mixture was poured into ice water, and extracted with ethyl acetate. The extracts were washed with water, and dried over magnesium sulfate. The extracts were filtered and concentrated under reduced pressure, and the resultant residue was purified by silica gel dry column chromatography to give 0.4 g of the intended product.

Yield: 10.6%, Properties: 107°-109° C.

The N-(substituted benzyloxy)imino derivatives of the general formula (1) are useful as agricultural and horticultural fungicides, and are very effective in controlling various plant diseases such as rice blast (*Pyricularia oryzae*), rice sheath blight (*Rhizoctonia solani*), rice brown spot (*Cochliobolus miyabeanus*), powdery mildew of barley (*Frysiphe graminis* f.sp. hordei) and other plants, rust of various plants, and the diseases caused by Oomycetes fungi such as tomato late blight (*Phytophthora infestans*) and cucumber downy mildw (*Pseudoperonaspora cubensis*).

The present inventive compounds have excellent activity in controlling diseases of paddy field crops, upland field crops, fruit trees, vegetables, other crops and flowering plants by the application to crop foliage, irrigation water or soil before or after disease appearance.

This invention however should not be limited to the these embodiments.

When the N-(substituted benzyloxy)imine derivative of the general formula (I) is used as an agricultural or horticultural fungicide, it is generally prepared into conveniently usable forms according to an ordinary manner for preparation of agrochemicals.

That is, the N-(substituted benzyloxy)imine derivative of the general formula (I) and, optionally, an adjuvant are blended with a suitable inert carrier and prepared into a suitable preparation form such as a suspension, emulsifiable concentrate, soluble concentrate, wettable powder, granules, dust or tablet through dissolution, dispersion, suspension, mixing, impregnation, adsorption or sticking.

The inert carrier in this invention may be solid or liquid. Examples of the solid carrier are soybean flour, cereal flour, wood flour, bark flour, saw dust, powdered tobacco stalks, powdered walnut shells, bran, powdered cellulose, extraction residues of vegetables, powdered synthetic polymers or resins, clays (e.g. kaolin, betonite, nd acid clay), talcs (e.g. talc and pyrophyllite), silica powders or flakes (e.g. diatomaceous earth, silica sand, mica and white carbon, i.e. synthetic, high-dispersion silicic acid, called finely divided hydrated silica or hydrated silicic acid), activated carbon, powdered sulfur, powdered pumice, calcined diatomaceous earth, ground brick, fly ash, sand, calcium carbonate powder, calcium phosphate powder and other inorganic or mineral powders, chemical fertilizers (e.g. ammonium sulfate, ammonium nitrate, urea and ammonium chloride), and compost. These carriers may be used alone or in combination.

The liquid carrier is that which itself has solubility or which is without such solubility but is capable of dispersing an active ingredient with the aid of an adjuvant. The following are typical examples of the liquid carrier and can be used alone or in combination. Water; alcohols such as methanol, ethanol, isopropanol, butanol and ethylene glycol; ketones such as acetone, methyl ethyl ketone, methyl isobutyl ketone, diisobutyl ketone and cyclohexanone; ethers such as ethyl ether, dioxane, Cellosolve, dipropyl ether and tetrahydrofuran; aliphatic hydrocarbons such as gasoline and mineral oils; aromatic hydrocarbons such as benzene, toluene, xylene, solvent naphtha and alkylnaphthalene; halogenated hydrocarbons such as dichloroethane, chloroform, carbon tetrachloride and chlorobenzene; esters such as ethyl acetate, diisopropyl phthalate, dibutyl phthalate and dioctyl phthalate; amides such as dimethylformamide and dimethylacetamide; nitriles such as acetonitrile; and dimethyl sulfoxide.

The following are typical examples of the adjuvant, which are used depending upon purpose and used alone or in combination in some cases, or may not be used at all.

To emulsify, disperse, dissolve and/or wet an active ingredient, a surfactant is used. Examples of the surfactant are polyoxyethylene alkyl ethers, polyoxyethylene alkylaryl ethers, polyoxyethylene higher fatty acid esters, polyoxyethylene resinates, polyoxyethylene sorbitan monolaurate, polyoxyethylene sorbitan monooleate, alkylarylsulfonates, naphthalenesulfonic acid condensation products, ligninsulfonates and higher alcohol sulfate esters.

Further, to stabilize the disersion of an active ingredient, tackify it and/or bind it, an adjuvant may be used. Example of such an adjuvant are casein, gelatin, starch, methylcellulose, carboxymethylcellulose, gum arabic, polyvinyl alcohol, turpentine, bran oil, bentonite and ligninsulfonates.

To improve the flowability of a solid product, an adjuvant may be used. Examples of such an adjuvant are waxes, stearates and alkyl phosphates.

Adjuvants such as naphthalenesulfonic acid condensation products and polycondensates of phosphates may be used as a peptizer for dispersible products.

Adjuvants, e.g. silicone oils, may be also used as a defoaming agent.

The content of the active ingredient may be varied as required. In dusts or granules, the suitable content thereof is from 0.1 to 50% by weight. In emulsifiable concentrates, flowable wettable powders, it is from 0.1 to 90% by weight.

An agricultural or horticultural fungicide containing the N-(substituted benzyloxy)imine derivative of the general formula (I) as an active ingredient is used to control a variety of crop diseases in the following manner. That is, it is applied to a crop on which diseases is estimated to occur or a site where occurrnece of diseases is undesirable directly or by suitably diluting it with water or suspending it in water in such an amount that is effective to control the diseases.

The amount of the agricultural or horticultural fungicide containing the N-(substituted benzyloxy)imine derivative of the general formula (I) as an active ingredient varies depending upon various factors such as a purpose, diseases to be controlled, a growth state of a plant, tendency of diseases occurrence, weather, environmental conditions, a preparation form, an application method, an application site and an application time. It is, however, used in an amount of 0.1 g to 1,000 g per 10 ares as an active ingredient depending upon a purpose.

The agricultural or horticultural fungicide containing the N-(substituted benzyloxy)imine derivative of the general formula (I) as an active ingredient may be used as a mixture thereof with an agrochemical, fertilizer and/or plant nutrient which are usable at its application time, or just in combination with these.

When the agricultural or horticultural fungicide containing the compound of this invention as an active ingredient is used to control crop diseases, it may be mixed with some other controller(s) to control other crop damage which occurs concurrently with crop diseases to be controlled by the present fungicide, and the mixture can be used as a multi-purpose controller. Examples of such other controller are as follows.

O,O-dimethyl O-(3-methyl-4-nitrophenyl)phosphorothioate (Fenitrothion)
O,O-dimethyl O-(3-methyl-4-methylthiophenyl)phosphorothioate (Fenthion)
S-α-ethoxycarbonylbenzyl O,O-dimethyl phosphorodithioate (Phenthioate)
O,O-diethyl O-(2-isopropyl-6-methyl-4-pyrimidinyl)-phosphorothioate (Diazinon)
dimethyl 2,2,2-trichloro-1-hydroxyethylphosphonate (Trichlorphon)
O-4-cyanophenyl O-ethyl phenylphosphonothioate (Cyanophenphos)
O-ethyl O-4-nitrophenyl phenylphosphonothioate (EPN)
4-(methylthio)phenyl dipropylphosphate (Propaphos)
O,O-dimethyl S-phthalimidomethyl phosphorodithioate (Phosmet)
2,2-dichlorovinyl dimethyl phosphate (DDVP)
O,O-dimethyl S-methylcarbamoylmethyl phosphorodithioate (Dimethoate)
S-1,2-bis(ethoxycarbonyl)ethyl O,O-dimethyl phosphorodithiate (Malathion)
1-naphthyl methylcarbamate (Carbaryl)
m-tolyl methylcarbamate (Metocarb)
2-isopropoxyphenyl methylcarbamate (propoxur)
S-(N-ethoxycarbonyl-N-methylcarbamoylmethyl) O,O-diethylphosphorodithioate (Mecarbam)
3,4-xylyl methylcarbamate (Xylylcarb)
2-sec-butylphenyl methylcarbamate (BPMC)
2-isopropylphenyl methylcarbamate (Isoprocarb)
2-chlorophenyl methylcarbamate (CPMC)
3,5-xylyl methylcarbamate (XMC)
2-(1,3-dioxolan-2-yl)phenyl methylcarbamate (Dioxacarb)
3-tert-butylphenyl methylcarbamate (Terbam)
4-diallylamino-3,5-xylyl methylcarbamate (Allyxycarb)
S-methyl N-(methylcarbamoyloxy)thioacetimidate (Methomyl)
N-(4-chloro-o-tolyl)-N,N-dimethylformamidine hydrochloride (Chlorodimeform)
1,3-bis-(carbamoylthio)-2-dimethylaminopropane hydrochloride (Cartap)
Diisopropyl 1,3-dithiolan-2-ylidenemalonate (Isoprothiolane)
S-benzyl O,O-diisopropyl phosphorothioate (IBP)

Following are typical Formulation Examples and Test Examples of this invention, which however shall not limit this invention.

In Formulation Examples, "part" stands for "part by weight".

FORMULATION EXAMPLE 1

| | |
|---|---|
| Compound No. 21 | 50 parts |
| Clay-white carbon mixture mainly containing clay | 45 parts |

| | |
|---|---|
| Polyoxyethylene nonylphenyl ether | 5 parts |

The above components were homogeneously mixed and pulverized to give a wettable powder.

FORMULATION EXAMPLE 2

| | |
|---|---|
| Compound No. 44 | 5 parts |
| Bentonite-clay mixture | 90 parts |
| Calcium lignin sulfonate | 5 parts |

The above components were homogeneously mixed, and the mixture was kneaded together with a suitable amount of water. The mixture was granulated and dried to give granules.

FORMULATION EXAMPLE 3

| | |
|---|---|
| Compound No. 96 | 50 parts |
| Xylene | 40 parts |
| Mixture of polyoxyethylene nonyl-phenyl ether with calcium alkyl-benzenesulfonate | 10 parts |

The above components were homogeneously mixed and dissolved to give an emulsifiable concentrate.

FORMULATION EXAMPLE 4

| | |
|---|---|
| Compound No. 201 | 3 parts |
| Powdered clay | 82 parts |
| Powdered diatomaceous earth | 15 parts |

The above components were homogeneously mixed and pulverized to give a dust.

FORMULATION EXAMPLE 5

| | |
|---|---|
| Compound No. 272 | 5 parts |
| Polyoxyethylene (10 moles) nonylphenyl ether | 1.4 parts |
| Polyoxyethylene styrenated phenol ether | 2 parts |
| Propylene glycol | 3 parts |
| Defoaming agent | 0.5 part |
| Heteropolysaccharide | 0.15 part |
| Water | 87.95 parts |

The above components were homogeneously mixed and pulverized to give a flowable preparation.

TEST EXAMPLE 1

Controlling effect on powdery mildew of barley (*Erysiphe graminis* f.s. hordei)

Barley seedlings at 2-leaf stage were sprayed with test compound (200 ppm) one day after inoculation with conidia of *Erysiphe graminis* f.sp. hordei. The seedlings were held in a constant-temperature room at 25° C. for one week and the percentage of the infected area per leaf was examined. Disease controlling activity was estimated in comparison with the untreated plot as follows.

| | |
|---|---|
| A: control rate | 100–95% |
| B: control rate | 94–80% |
| C: control rate | 79–60% |
| D: control rate | 59–0% |

TABLE 2

| Compound No. | Fungicidal effect |
|---|---|
| 1 | A |
| 2 | C |
| 3 | B |
| 4 | A |
| 5 | C |
| 6 | A |
| 7 | A |
| 9 | A |
| 10 | A |
| 11 | A |
| 12 | A |
| 13 | A |
| 14 | A |
| 15 | A |
| 16 | A |
| 17 | A |
| 21 | A |
| 22 | A |
| 23 | A |
| 24 | A |
| 25 | A |
| 26 | A |
| 27 | A |
| 28 | A |
| 29 | A |
| 30 | A |
| 31 | A |
| 32 | A |
| 33 | A |
| 34 | A |
| 35 | A |
| 36 | A |
| 38 | A |
| 39 | A |
| 40 | A |
| 41 | A |
| 42 | A |
| 43 | A |
| 44 | A |
| 47 | A |
| 48 | A |
| 49 | A |
| 50 | B |
| 51 | A |
| 52 | A |
| 55 | A |
| 56 | A |
| 57 | C |
| 59 | A |
| 60 | A |
| 61 | C |
| 65 | C |
| 66 | A |
| 67 | A |
| 68 | A |
| 69 | A |
| 70 | A |
| 71 | B |
| 72 | B |
| 74 | A |
| 75 | A |
| 78 | B |
| 79 | A |
| 80 | C |
| 81 | A |
| 82 | A |
| 83 | B |
| 84 | B |
| 87 | A |
| 88 | A |
| 89 | B |
| 91 | A |
| 92 | A |
| 93 | A |
| 94 | A |
| 95 | A |

TABLE 2-continued

| Compound No. | Fungicidal effect |
|---|---|
| 96 | A |
| 97 | C |
| 98 | A |
| 102 | A |
| 103 | B |
| 105 | B |
| 106 | B |
| 107 | A |
| 108 | A |
| 109 | A |
| 110 | A |
| 111 | B |
| 112 | B |
| 113 | A |
| 114 | A |
| 115 | A |
| 116 | A |
| 117 | A |
| 118 | A |
| 119 | A |
| 120 | A |
| 121 | A |
| 122 | A |
| 123 | A |
| 124 | A |
| 125 | A |
| 126 | A |
| 127 | A |
| 128 | B |
| 129 | A |
| 130 | A |
| 131 | A |
| 132 | A |
| 133 | A |
| 134 | A |
| 135 | A |
| 137 | A |
| 139 | A |
| 141 | B |
| 142 | A |
| 143 | A |
| 144 | A |
| 145 | C |
| 146 | A |
| 147 | A |
| 148 | A |
| 149 | A |
| 150 | A |
| 151 | A |
| 152 | A |
| 153 | B |
| 154 | A |
| 155 | A |
| 156 | B |
| 157 | A |
| 158 | A |
| 159 | A |
| 160 | A |
| 161 | A |
| 162 | A |
| 163 | A |
| 164 | A |
| 165 | A |
| 166 | A |
| 167 | A |
| 168 | A |
| 169 | A |
| 170 | C |
| 171 | A |
| 172 | A |
| 173 | A |
| 174 | A |
| 175 | C |
| 176 | A |
| 177 | A |
| 178 | A |
| 179 | C |
| 180 | A |
| 181 | B |
| 182 | A |
| 183 | A |

TABLE 2-continued

| Compound No. | Fungicidal effect |
|---|---|
| 184 | A |
| 185 | A |
| 186 | A |
| 187 | C |
| 188 | A |
| 189 | A |
| 190 | A |
| 191 | A |
| 192 | A |
| 193 | A |
| 194 | A |
| 197 | A |
| 198 | A |
| 199 | A |
| 200 | B |
| 201 | A |
| 202 | A |
| 203 | A |
| 204 | A |
| 205 | C |
| 206 | A |
| 207 | B |
| 208 | A |
| 209 | B |
| 210 | A |
| 211 | A |
| 212 | A |
| 213 | A |
| 215 | B |
| 216 | B |
| 217 | A |
| 218 | A |
| 219 | A |
| 220 | B |
| 221 | C |
| 223 | A |
| 225 | A |
| 226 | A |
| 227 | A |
| 228 | A |
| 229 | A |
| 230 | A |
| 231 | A |
| 232 | A |
| 233 | A |
| 234 | A |
| 235 | A |
| 236 | A |
| 237 | B |
| 238 | A |
| 239 | A |
| 240 | A |
| 241 | A |
| 242 | A |
| 243 | A |
| 244 | A |
| 245 | A |
| 246 | A |
| 247 | A |
| 248 | C |
| 249 | A |
| 253 | A |
| 254 | A |
| 255 | A |
| 256 | A |
| 257 | A |
| 258 | A |
| 259 | C |
| 260 | C |
| 265 | C |
| 268 | C |
| 271 | A |
| 272 | A |
| 273 | A |
| 274 | A |
| 275 | A |
| 276 | A |
| 277 | A |
| 278 | A |
| 279 | A |
| 280 | A |

TABLE 2-continued

| Compound No. | Fungicidal effect |
|---|---|
| 281 | B |
| 282 | A |
| 283 | A |
| 284 | A |
| 285 | A |
| 286 | A |
| 287 | A |
| 288 | A |
| 289 | A |
| 290 | A |
| 291 | A |
| 292 | A |
| 293 | A |
| 294 | A |
| 295 | A |
| 296 | A |
| 297 | A |
| 298 | A |
| 299 | A |
| 300 | A |
| 301 | A |
| 302 | A |
| 303 | A |
| 304 | A |
| 305 | C |
| 306 | C |
| 307 | A |
| 308 | A |
| 309 | B |
| 310 | C |
| 311 | B |
| 312 | A |
| 313 | A |
| 314 | A |
| 315 | A |
| 316 | A |
| 317 | B |
| 318 | A |
| 319 | C |
| 321 | A |
| 322 | B |
| 323 | A |
| 326 | C |
| 327 | A |
| 327 | C |
| 328 | C |
| 329 | A |
| 330 | A |
| 331 | A |
| 332 | A |
| 333 | A |
| 334 | A |
| 335 | A |
| 336 | A |
| 337 | C |
| 338 | A |
| 339 | A |
| 340 | A |
| 341 | A |
| 342 | A |
| 343 | A |
| 344 | C |
| 345 | A |
| 346 | A |
| 347 | A |
| 348 | A |
| 349 | A |
| 350 | A |
| 351 | B |
| 351 | B |
| 352 | A |
| 353 | A |
| 354 | A |
| 355 | A |
| 356 | A |
| 357 | A |
| 358 | A |
| 359 | A |
| 360 | A |
| 361 | A |
| 362 | A |
| 363 | A |
| 365 | A |
| 366 | C |
| 368 | A |
| 369 | A |
| 370 | A |
| 371 | A |
| 372 | A |
| 374 | B |
| 379 | A |
| 380 | A |
| 381 | A |
| 382 | A |
| 383 | A |
| 384 | A |
| 385 | A |
| 386 | A |
| 387 | A |
| 388 | A |
| 389 | A |
| 390 | A |
| 391 | A |
| 392 | A |
| 393 | A |
| 394 | A |
| 396 | A |
| 397 | A |
| 398 | A |
| 399 | A |
| 400 | A |
| 401 | B |
| 402 | A |
| 403 | A |
| 400 | A |
| 404 | A |
| 405 | A |
| 406 | A |
| 407 | A |
| Reference Compound A | D |
| Reference Compound B | D |
| Reference Compound C | C |

Note:
Reference Compound A: Compound of JP, A 61-280452

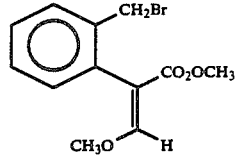

Reference Compound B: Compound of JP, A 61-106538

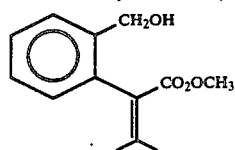

Reference Compound D: Compound of JP, A 61-106538

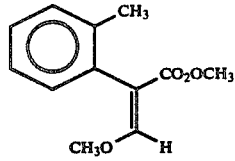

TEST EXAMPLE 2

Controlling effect on downy mildew of cucumber (*Pseudoperonospora cubensis*)

Cucumber plants at 2-leaf stage were sprayed with test compound (200 ppm) one day before inoculation with zoospores of *Pseudoperonospora cubensis*. After the plants were held in a humid room at 25° C. for one day and then in a greenhouse for 6 days, the degree of infection per leaf was examined. Disease controlling activity was estimated in the same manner as in Test example 1. The results are shown in Table 3.

TABLE 3

| Compound No. | Fungicidal effect |
|---|---|
| 1 | A |
| 2 | B |
| 3 | A |
| 5 | B |
| 6 | C |
| 9 | C |
| 10 | A |
| 11 | B |
| 12 | A |
| 13 | B |
| 14 | A |
| 15 | A |
| 16 | B |
| 17 | B |
| 20 | A |
| 21 | A |
| 22 | A |
| 23 | A |
| 24 | A |
| 25 | A |
| 27 | A |
| 28 | B |
| 29 | A |
| 30 | A |
| 31 | A |
| 32 | A |
| 33 | A |
| 34 | A |
| 35 | A |
| 40 | A |
| 41 | A |
| 42 | B |
| 43 | B |
| 44 | A |
| 45 | C |
| 47 | C |
| 48 | A |
| 49 | B |
| 52 | B |
| 53 | C |
| 55 | A |
| 56 | C |
| 58 | C |
| 59 | A |
| 61 | B |
| 62 | C |
| 66 | A |
| 67 | A |
| 68 | A |
| 69 | B |
| 70 | A |
| 71 | B |
| 74 | C |
| 75 | B |
| 77 | C |
| 78 | B |
| 79 | A |
| 80 | C |
| 81 | A |
| 82 | A |
| 83 | A |
| 86 | B |
| 91 | B |
| 92 | A |
| 93 | A |
| 95 | B |
| 96 | B |
| 97 | A |
| 104 | C |
| 105 | A |
| 106 | A |
| 107 | B |

TABLE 3-continued

| Compound No. | Fungicidal effect |
|---|---|
| 109 | A |
| 110 | A |
| 111 | A |
| 112 | B |
| 114 | A |
| 115 | B |
| 118 | A |
| 119 | A |
| 120 | A |
| 122 | A |
| 124 | A |
| 125 | A |
| 126 | A |
| 127 | A |
| 128 | A |
| 129 | C |
| 131 | C |
| 132 | C |
| 133 | A |
| 134 | A |
| 135 | A |
| 137 | A |
| 139 | B |
| 142 | C |
| 143 | A |
| 144 | A |
| 145 | B |
| 146 | A |
| 147 | A |
| 148 | A |
| 149 | A |
| 150 | A |
| 151 | A |
| 152 | A |
| 153 | A |
| 154 | A |
| 155 | A |
| 156 | A |
| 157 | A |
| 158 | A |
| 159 | A |
| 160 | A |
| 161 | A |
| 162 | C |
| 163 | A |
| 164 | A |
| 165 | A |
| 167 | A |
| 168 | A |
| 169 | A |
| 170 | C |
| 172 | A |
| 174 | A |
| 175 | A |
| 176 | A |
| 177 | A |
| 178 | A |
| 179 | A |
| 181 | A |
| 185 | A |
| 186 | A |
| 187 | B |
| 188 | A |
| 190 | A |
| 193 | C |
| 198 | A |
| 199 | A |
| 200 | A |
| 201 | A |
| 202 | C |
| 203 | A |
| 204 | A |
| 205 | B |
| 206 | A |
| 207 | A |
| 208 | A |
| 216 | B |
| 218 | C |
| 219 | A |
| 220 | A |

TABLE 3-continued

| Compound No. | Fungicidal effect |
|---|---|
| 221 | A |
| 222 | A |
| 223 | A |
| 224 | A |
| 225 | A |
| 226 | A |
| 227 | A |
| 228 | A |
| 229 | A |
| 230 | A |
| 231 | A |
| 232 | A |
| 233 | A |
| 234 | A |
| 235 | A |
| 236 | A |
| 237 | A |
| 238 | A |
| 239 | A |
| 240 | A |
| 241 | A |
| 242 | C |
| 243 | A |
| 244 | A |
| 245 | A |
| 246 | A |
| 247 | C |
| 248 | A |
| 249 | A |
| 250 | A |
| 255 | A |
| 256 | A |
| 257 | B |
| 258 | B |
| 259 | A |
| 260 | A |
| 261 | C |
| 262 | C |
| 263 | C |
| 264 | B |
| 266 | B |
| 269 | B |
| 271 | A |
| 272 | A |
| 273 | A |
| 274 | A |
| 275 | B |
| 276 | B |
| 277 | A |
| 278 | A |
| 279 | A |
| 281 | A |
| 282 | A |
| 283 | A |
| 284 | A |
| 285 | A |
| 286 | A |
| 287 | A |
| 288 | B |
| 289 | C |
| 290 | A |
| 291 | A |
| 292 | A |
| 293 | A |
| 294 | A |
| 295 | A |
| 296 | A |
| 298 | B |
| 299 | C |
| 300 | A |
| 301 | A |
| 302 | A |
| 303 | A |
| 304 | A |
| 306 | C |
| 307 | A |
| 308 | C |
| 309 | B |
| 313 | A |
| 314 | A |
| 315 | A |
| 316 | A |
| 317 | B |
| 318 | A |
| 319 | A |
| 321 | A |
| 323 | A |
| 324 | A |
| 325 | B |
| 326 | A |
| 329 | B |
| 330 | A |
| 331 | B |
| 332 | A |
| 333 | C |
| 334 | A |
| 336 | A |
| 338 | A |
| 339 | A |
| 340 | A |
| 341 | A |
| 342 | A |
| 343 | B |
| 344 | A |
| 345 | A |
| 347 | A |
| 348 | A |
| 349 | A |
| 350 | A |
| 351 | A |
| 352 | A |
| 353 | A |
| 354 | A |
| 355 | A |
| 356 | A |
| 357 | A |
| 358 | A |
| 360 | A |
| 361 | A |
| 363 | A |
| 364 | B |
| 365 | A |
| 366 | B |
| 367 | C |
| 368 | A |
| 370 | A |
| 371 | A |
| 372 | C |
| 374 | C |
| 379 | B |
| 380 | B |
| 381 | B |
| 384 | A |
| 385 | A |
| 386 | A |
| 387 | A |
| 388 | A |
| 389 | A |
| 391 | A |
| 392 | A |
| 393 | A |
| 394 | B |
| 396 | A |
| 397 | A |
| 399 | A |
| 400 | A |
| 401 | C |

TEST EXAMPLE 3

Controlling effect on rice blast (*Pyricularia oryzae*)

Rice seedling at 5-leaf stage were sprayed with test compound (200 ppm) one day before inoculation with conidia of *Pyricularia oryzae*. After the seedlings were held in a humid room at 25° C. for one day and then held in a greenhouse for 6 days, the number of lesions appeared per leaf was examined. Disease controlling activity was estimated in the same manner as in Test example 1. The results are shown in Table 4.

TABLE 4

| Compound No. | Fungicidal effect |
|---|---|
| 1 | A |
| 2 | B |
| 3 | A |
| 4 | C |
| 6 | A |
| 9 | C |
| 10 | B |
| 11 | A |
| 12 | B |
| 13 | A |
| 14 | A |
| 15 | A |
| 16 | A |
| 17 | C |
| 19 | B |
| 20 | C |
| 21 | A |
| 22 | C |
| 23 | A |
| 24 | A |
| 25 | A |
| 26 | A |
| 27 | A |
| 28 | A |
| 29 | A |
| 30 | A |
| 31 | A |
| 32 | B |
| 33 | A |
| 34 | A |
| 35 | A |
| 36 | A |
| 39 | B |
| 40 | A |
| 41 | A |
| 42 | A |
| 43 | A |
| 44 | A |
| 46 | C |
| 47 | C |
| 48 | A |
| 49 | A |
| 50 | B |
| 51 | B |
| 52 | A |
| 53 | C |
| 55 | A |
| 56 | C |
| 57 | C |
| 59 | A |
| 60 | C |
| 66 | C |
| 67 | A |
| 68 | A |
| 69 | B |
| 70 | C |
| 71 | C |
| 72 | A |
| 73 | C |
| 75 | A |
| 77 | C |
| 78 | B |
| 79 | A |
| 80 | A |
| 81 | A |
| 82 | A |
| 83 | A |
| 84 | A |
| 86 | A |
| 87 | C |
| 88 | C |
| 89 | A |
| 90 | C |
| 92 | A |
| 93 | A |
| 94 | B |

TABLE 4-continued

| Compound No. | Fungicidal effect |
|---|---|
| 96 | A |
| 97 | B |
| 98 | A |
| 101 | C |
| 102 | B |
| 103 | A |
| 104 | C |
| 105 | A |
| 106 | A |
| 107 | A |
| 109 | A |
| 110 | A |
| 111 | A |
| 112 | A |
| 113 | A |
| 114 | A |
| 115 | A |
| 116 | B |
| 118 | A |
| 119 | A |
| 120 | A |
| 121 | B |
| 122 | A |
| 123 | A |
| 124 | A |
| 125 | A |
| 126 | A |
| 127 | A |
| 128 | A |
| 129 | A |
| 130 | A |
| 131 | A |
| 132 | A |
| 133 | A |
| 134 | A |
| 135 | A |
| 136 | A |
| 137 | A |
| 138 | A |
| 139 | A |
| 140 | A |
| 141 | A |
| 142 | A |
| 143 | A |
| 144 | A |
| 145 | A |
| 146 | A |
| 147 | A |
| 148 | A |
| 149 | A |
| 150 | A |
| 151 | A |
| 152 | A |
| 153 | A |
| 154 | A |
| 155 | A |
| 156 | A |
| 157 | A |
| 158 | A |
| 159 | A |
| 160 | B |
| 161 | B |
| 162 | C |
| 163 | A |
| 164 | A |
| 165 | A |
| 166 | A |
| 167 | A |
| 168 | A |
| 169 | A |
| 170 | A |
| 171 | A |
| 172 | A |
| 173 | C |
| 174 | A |
| 175 | B |
| 176 | A |
| 177 | A |
| 178 | A |
| 179 | A |

TABLE 4-continued

| Compound No. | Fungicidal effect |
|---|---|
| 180 | A |
| 181 | A |
| 182 | B |
| 183 | A |
| 184 | A |
| 185 | A |
| 186 | A |
| 187 | A |
| 188 | A |
| 189 | A |
| 190 | A |
| 191 | A |
| 192 | A |
| 193 | C |
| 194 | A |
| 197 | A |
| 198 | A |
| 199 | A |
| 200 | A |
| 201 | A |
| 202 | A |
| 203 | A |
| 204 | A |
| 205 | B |
| 206 | A |
| 207 | A |
| 208 | A |
| 209 | A |
| 210 | A |
| 211 | A |
| 212 | A |
| 213 | A |
| 214 | C |
| 215 | B |
| 216 | A |
| 217 | B |
| 218 | A |
| 219 | A |
| 220 | A |
| 221 | B |
| 222 | C |
| 223 | A |
| 224 | A |
| 225 | A |
| 226 | A |
| 227 | A |
| 228 | A |
| 229 | A |
| 230 | A |
| 231 | A |
| 232 | A |
| 233 | A |
| 234 | B |
| 235 | A |
| 236 | A |
| 237 | A |
| 238 | A |
| 239 | B |
| 240 | A |
| 241 | A |
| 242 | A |
| 243 | A |
| 244 | A |
| 245 | A |
| 246 | A |
| 247 | A |
| 248 | B |
| 249 | A |
| 250 | A |
| 253 | A |
| 254 | A |
| 255 | A |
| 256 | A |
| 257 | A |
| 258 | A |
| 259 | A |
| 260 | A |
| 261 | C |
| 263 | C |
| 265 | A |
| 266 | A |
| 271 | B |
| 272 | A |
| 273 | A |
| 274 | A |
| 275 | A |
| 276 | A |
| 277 | A |
| 278 | A |
| 279 | A |
| 280 | A |
| 281 | B |
| 282 | A |
| 283 | A |
| 284 | A |
| 285 | A |
| 286 | A |
| 287 | A |
| 288 | A |
| 289 | A |
| 290 | A |
| 292 | A |
| 293 | A |
| 294 | A |
| 295 | A |
| 296 | A |
| 297 | B |
| 298 | A |
| 299 | A |
| 300 | A |
| 301 | A |
| 302 | A |
| 303 | A |
| 304 | A |
| 305 | A |
| 306 | A |
| 307 | A |
| 308 | A |
| 309 | A |
| 310 | A |
| 311 | C |
| 312 | A |
| 313 | A |
| 314 | A |
| 315 | A |
| 316 | A |
| 317 | C |
| 318 | A |
| 319 | A |
| 320 | A |
| 321 | A |
| 322 | A |
| 323 | A |
| 324 | B |
| 327 | A |
| 328 | B |
| 329 | A |
| 330 | A |
| 331 | A |
| 332 | A |
| 333 | C |
| 334 | A |
| 335 | A |
| 336 | A |
| 337 | B |
| 338 | A |
| 339 | A |
| 340 | A |
| 341 | A |
| 342 | A |
| 343 | A |
| 344 | A |
| 345 | A |
| 346 | A |
| 347 | A |
| 348 | A |
| 349 | A |
| 350 | A |
| 351 | B |
| 352 | A |

TABLE 4-continued

| Compound No. | Fungicidal effect |
|---|---|
| 353 | A |
| 354 | B |
| 355 | A |
| 356 | A |
| 357 | A |
| 358 | A |
| 359 | A |
| 360 | A |
| 361 | A |
| 362 | A |
| 363 | A |
| 364 | A |
| 365 | A |
| 366 | A |
| 369 | A |
| 370 | A |
| 371 | A |
| 372 | A |
| 373 | B |
| 374 | B |
| 375 | B |
| 376 | B |
| 379 | A |
| 380 | A |
| 381 | A |
| 382 | A |
| 383 | A |
| 385 | B |
| 386 | A |
| 387 | A |
| 388 | A |
| 389 | C |
| 391 | A |
| 392 | A |
| 393 | A |
| 394 | A |
| 396 | A |
| 397 | A |
| 398 | A |
| 399 | A |
| 400 | A |
| 401 | A |
| 402 | A |
| 403 | A |
| 404 | A |
| 405 | A |
| 406 | B |
| 407 | A |
| 408 | C |
| Reference Compound A | D |
| Reference Compound B | D |
| Reference Compound C | C |

What is claimed is:

1. N-(substituted benzyloxy)imine derivatives of general formula

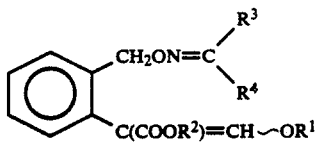

wherein
R$^1$ and R$^2$ each independently represent a C$_1$-C$_3$ alkyl group;
one of R$^3$ and R$^4$ presents a C$_1$-C$_3$ alkyl group, a haloalkyl group having one to three carbon atoms, a C$_1$-C$_3$ alkoxy-C$_1$-C$_3$ alkyl group or a benzyloxy group; and the other is a nitrogen atom-containing hetero ring selected from the group consisting of substituted or unsubstituted pyrrolidine, piperidine, morpholine, thiomorpholine, piperizine, hexamethyleneimine, tetrahydroquinoline and tetrahydroisoquinoline whose nitrogen atoms always forms the bond with either a substituent R$^3$ or R$^4$; said hetero ring may have independently as a substituents(s) 1 or more of halogen atoms, C$_1$-C$_3$ alkyl groups, phenyl groups, benzyl groups, pyridyl groups, pyrimidyl groups or 1,3-dioxolane groups which may be substituted independently with 1-5 halogen atoms.

2. The N-(substituted benzyloxy)imine derivatives of claim 1 wherein one of R$^3$ and R$^4$ is a C$_1$-C$_3$ alkyl group or a C$_1$-C$_3$ alkoxy C$_1$-C$_3$ alkyl group and the other is a hetero ring selected from the group consisting of substituted or unsubstituted-pyrrolidine, piperidine, morpholine, thiomorpholine, piperazine, hexamethyleneimine, tetrahydroquinoline and tetrahydroisoquinoline; said hetero ring may have independently as a substituent(s) 1 or more alkyl groups.

3. The N-(substituted benzyloxy)imine derivatives of claim 2 wherein said one of R$^3$ and R$^4$ is a C$_1$-C$_3$ alkyl group and the other is a morpholine group which may have as a substituent(s) independently one or more C$_1$-C$_3$ alkyl group.

4. The compound of general formula

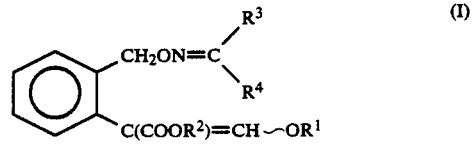

wherein
R$^1$ and R$^2$ are C$_1$-C$_3$ alkyl group;
either R$^3$ and R$^4$ is a C$_1$-C$_3$ alkyl group; a haloalkyl group having one to three carbon atoms, C$_1$-C$_3$ alkoxy C$_1$-C$_3$ alkyl group or a benzyloxy group, and the other R$^3$ or R$^4$ is a nitrogen atom-containing hetero ring selected from the group consisting of pyrrolidine, piperidine, morpholine, thiomorpholine, piperizine, hexamethyleneimine, tetrahydroquinoline and tetrahydroisoquinoline whose nitrogen atom bonds as R$^3$ or R$^4$, wherein said hetero ring is unsubstituted or substituted with at least one member selected from the group consisting of a C$_1$-C$_3$ alkyl group phenyl group, a benzyl group, a pyridyl group, a pyrimidyl group a 1,3 dioxolane group, and a halogenated 1,3 dioxolane group.

5. The compound of claim 4 wherein said hetero ring is substituted with at least one alkyl group.

6. The compound of claim 4 wherein said hetero ring is unsubstituted.

7. The compound of claim 4 wherein the hetero ring is morpholine.

8. The compound of claim 7 wherein the morpholine group is cis- or trans-substituted with a C$_1$-C$_3$ alkyl group.

9. The compound of claim 8 wherein the morpholine group is cis- or trans-2,6-dimethyl morpholino.

10. An agricultural or horticultural fungicide which comprises a fungicidally effective amount of the compound of claim 4 and an agriculturally or horticulturally acceptable carrier.

11. An agricultural or horticultural fungicide which comprises a fungicidally effective amount of the compound of claim 5 and an agriculturally or horticulturally acceptable carrier.

12. An agricultural or horticultural fungicide which comprises a fungicidally effective amount of the compound of claim 8 and an agriculturally or horticulturally acceptable carrier.

13. A method of controlling fungal growth on plants or plant products comprising applying the fungicide of claim 10 to a plant or plant material.

14. A method of controlling fungal growth on plants or plant products comprising applying the fungicide of claim 11 to a plant or plant material.

15. A method of controlling fungal growth on plants or plant products comprising applying the fungicide of claim 12 to a plant or plant material.

16. The method of claim 15 further comprising applying between 0.1 and 1,000 grams of fungicide per 10 hectares.

17. The method of claim 14 further comprising applying between 0.1 and 1,000 grams of fungicide per 10 hectares.

18. The method of claim 15 further comprising applying between 0.1 and 1,000 grams of fungicide per 10 hectares.

* * * * *